(12) United States Patent
Olivo et al.

(10) Patent No.: US 11,237,159 B2
(45) Date of Patent: Feb. 1, 2022

(54) SURFACE ENHANCED RAMAN SPECTROSCOPY (SERS) MICROFLUIDICS BIOSENSOR FOR DETECTING SINGLE AND/OR MULTIPLE ANALYTES

(71) Applicant: Agency for Science, Technology and Research, Singapore (SG)

(72) Inventors: Malini Olivo, Singapore (SG); Jayakumar Perumal, Singapore (SG); Ghayathri Balasundaram, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 454 days.

(21) Appl. No.: 16/086,285

(22) PCT Filed: Mar. 23, 2017

(86) PCT No.: PCT/SG2017/050144
§ 371 (c)(1),
(2) Date: Sep. 18, 2018

(87) PCT Pub. No.: WO2017/164815
PCT Pub. Date: Sep. 28, 2017

(65) Prior Publication Data
US 2020/0292538 A1    Sep. 17, 2020

(30) Foreign Application Priority Data

Mar. 23, 2016  (SG) .......................... 10201602281Y

(51) Int. Cl.
*G01N 33/543*   (2006.01)
*B01L 3/00*   (2006.01)
(Continued)

(52) U.S. Cl.
CPC .. *G01N 33/54373* (2013.01); *B01L 3/502707* (2013.01); *B01L 3/502715* (2013.01);
(Continued)

(58) Field of Classification Search
CPC ............ G01N 33/54373; G01N 21/658; B01L 3/502715; B01L 3/502707; B01L 2300/16; B01L 2200/0647
See application file for complete search history.

(56) References Cited

U.S. PATENT DOCUMENTS

2003/0059820 A1* 3/2003 Vo-Dinh .............. C12Q 1/6837
506/3
2015/0253321 A1* 9/2015 Chou ............... G01N 33/54386
435/5

FOREIGN PATENT DOCUMENTS

CN   104422769 A    3/2015
WO   2011078794 A1   6/2011
(Continued)

OTHER PUBLICATIONS

Extended European Search Report for European Patent Application No. 17 770 724.7 dated Oct. 4, 2019, pp. 1-10.
(Continued)

*Primary Examiner* — Jennifer Wecker
*Assistant Examiner* — Kathryn Elizabeth Limbaugh
(74) *Attorney, Agent, or Firm* — Winstead PC

(57) ABSTRACT

A biosensor for the detection of an analyte using surface-enhanced Raman spectroscopy (SERS) is provided. The biosensor includes a SERS-active substrate and a microfluidic circuit device arranged to be in fluid communication with the SERS-active substrate. Method of manufacturing a biosensor, and methods for detecting an analyte using the biosensor, wherein the analyte may be haptoglobin, are also provided.

18 Claims, 13 Drawing Sheets

(51) Int. Cl.
   G01N 21/65 (2006.01)
   G01N 33/574 (2006.01)
(52) U.S. Cl.
   CPC ...... B01L 3/502761 (2013.01); G01N 21/658
          (2013.01); G01N 33/57449 (2013.01); B01L
              2200/0647 (2013.01); B01L 2200/12
              (2013.01); B01L 2300/16 (2013.01)

(56) References Cited

FOREIGN PATENT DOCUMENTS

| WO | 2014055559 A1 | 4/2014 |
|---|---|---|
| WO | 2016036410 A1 | 3/2016 |

OTHER PUBLICATIONS

Huang et al., "SERS-Enabled Lab-on-a-Chip Systems," Advanced Optical Materials, vol. 3, No. 5, May 23, 2015, pp. 318-633.
Lagus et al., "A Review of the Theory, Methods and Recent Applications of High-Throughput Single-Cell Droplet Microfluidics," Journal of Physics D: Applied Physics, vol. 46, No. 11, Feb. 22, 2013, pp. 1-21.
Zhou et al., "Review of Microfluidic Approaches for Surface-Enhanced Raman Scattering," Sensors and Actuators B Chemical, vol. 227, May 2016, pp. 504-514, See Abstract.
Hong et al., "A Concentration Gradient Generator on a Paper-Based Microfluidic Chip Coupled with Cell Culture Microarray for High-Throughput Drug Screening," Biomed Microdevices, vol. 18, No. 21, Feb. 11, 2016, pp. 1-8.
Escobedo et al., "Quantification of Ovarian Cancer Markers with Integrated Microfluidic Concentration Gradient and Imaging Nanohole Surface Plasmon Resonance," Analyst, vol. 138, No. 5, 2013, pp. 1450-1458.
Perumal et al., "Design and Fabrication of Random Silver Films as Substrate for SERS Based Nano-Stress Sensing of Proteins," RSC Advances, vol. 4, No. 25, 2014, pp. 12995-13000.
Geng et al., "A Route to Apply Ag Nanoparticle Array Integrated with Microfluidic for Surface Enhanced Raman Scattering," Sensors and Actuators A: Physical, vol. 169, 2011, pp. 37-42.
Ku et al., "A SERS-Active Microfluidic Device with Tunable Surface Plasmon Resonances," Electrophoresis, vol. 32, 2011, pp. 3378-3384.
Kim et al., "Microfluidic-SERS Devices for One Shot Limit-of-Detection," Analyst, vol. 139, No. 13, Jul. 7, 2014, pp. 3227-3234.
Ackermann et al., "Quantitative Online Detection of Low-Concentrated Drugs via a SERS Microfluidic System," ChemPhysChem, vol. 8, 2007, pp. 2665-2670.
Oh et al., "Optofluidic SERS Chip with Plasmonic Nanoprobes Self-Aligned Along Microfluidic Channels," Lab Chip, vol. 14, 2014, pp. 865-868.
Owens et al., "Sensing of p53 and EGFR Biomarkers Using High Efficiency SERS Substrates," Biosensors, vol. 5, 2015, pp. 664-677.
Perumal et al., "SERS-Based Quantitative Detection of Ovarian Cancer Prognostic Factor Haptoglobin," International Journal of Nanomedicine, vol. 10, 2015, pp. 1831-1840.
Kim et al., "Development of a Novel Low-Cost Au-Printed SERS Paper Substrate for Point-of-Care Application," IEEE International Conference on Advanced Intelligent Mechatronics (AIM), Busan, Korea, Jul. 7-11, 2015, pp. 535-536.
Li et al., "Multiplexed Detection of Serological Cancer Markers with Plasmon-Enhanced Raman Spectro-mmunoassay," Chemical Science, vol. 6, 2015, pp. 3906-3914.
International Preliminary Report on Patentability for International Application No. PCT/SG2017/050144 dated May 21, 2018, pp. 1-23.

\* cited by examiner

Experimental data

Simulated data

| Microchannel | Raman Intensity | Estimated 2-NT conc. (uM) [Simulation Data] |
|---|---|---|
| 1 | 50126 | 9.55 |
| 2 | 32658 | 8.13 |
| 3 | 11740 | 6.78 |
| 4 | 5553 | 4.39 |
| 5 | 710 | 2.01 |

SURFACE ENHANCED RAMAN SPECTROSCOPY (SERS) MICROFLUIDICS BIOSENSOR FOR DETECTING SINGLE AND/OR MULTIPLE ANALYTES

CROSS-REFERENCE TO RELATED APPLICATION

This application claims the benefit of priority of Singapore patent application No. 10201602281Y filed on 23 Mar. 2016, the content of which is incorporated herein by reference in its entirety for all purposes.

TECHNICAL FIELD

Various embodiments relate to a biosensor for the detection of analyte using surface-enhanced Raman spectroscopy (SERS), method of manufacturing the biosensor, and method for detecting an analyte such as haptoglobin (Hp) using the biosensor.

BACKGROUND

In medical practice, for example, identification of a disease requires recognition of associated symptoms, as well as detection of specific features that indicate its presence unambiguously.

Identification of a disease may be carried out through biomarker screening, which may only be carried out through an analysis of biological fluids, such as blood, urine and cerebral spinal fluid. An accurate diagnostic may rarely be accomplished through detection of a single biomarker, hence a panel of markers has to be analyzed for reliable results, such as in a multiplexed assay. Monitoring the expression patterns of a variety of biomarkers at various stages of a disease assists prognosis, and allows tracking of disease progression. Early detection in asymptomatic populations is of utmost importance to facilitate early treatment and to reduce health-care costs.

State of the art protein biomarker assays are largely based on immunoassays. Platforms made of polymer or glass and bearing several immobilized antibodies spotted on different well-defined locations are usually provided. These assays involve exposure of the platform to the sample, followed by incubation with one or two further antibodies, and several washing and blocking steps in between to increase specificity of the assay results. Detection is usually via fluorescence detection, chromophoric absorption, or a colorimetric readout.

Although a number of immunosensor arrays have been developed in recent years, a truly rapid, accurate and miniaturizable system is still non-existent. Taking Enzyme-linked immunosorbent assay (ELISA), for example, it is the current gold standard for bio-assay. Each ELISA analysis requires a separate distinct reaction and, in addition, requires a label for detection of the analyte. It is a biochemical technique used mainly in immunology to detect the presence of an antibody or an antigen in a sample. It uses two antibodies. One antibody is specific to the antigen. The other reacts to antigen-antibody complexes, and is coupled to an enzyme. Due to the presence of peroxidase enzyme in the secondary antibody, peroxidase reaction takes place in presence of peroxidase substrate such as TMB ($3,3^0,5,5^0$-Tetramethylbenzidine), which leads to a product which can be detected by UV absorbance. However, it requires multiple steps, each with separate reagents. It is therefore time consuming and labor intensive, and the results are also highly dependent on the operator skill.

In view of the above, there exists a need for an improved method and device for the detection of an analyte that overcomes or at least alleviates one or more of the above problems.

SUMMARY

In a first aspect, a biosensor for the detection of an analyte using surface-enhanced Raman spectroscopy (SERS) is provided. The biosensor comprises a SERS-active substrate and a microfluidic circuit device arranged to be in fluid communication with the SERS-active substrate.

In a second aspect, a method of manufacturing a biosensor for the detection of an analyte using surface-enhanced Raman spectroscopy (SERS) according to the first aspect is provided. The method comprises
  a) providing a SERS-active substrate, and
  b) arranging a microfluidic circuit device to be in fluid communication with the SERS-active substrate to obtain the biosensor.

In a third aspect, a method for detecting at least one analyte using surface enhanced Raman spectroscopy (SERS) is provided. The method comprises
  a) providing a biosensor according to the first aspect;
  b) introducing at least one analyte binding molecule to the microfluidic circuit device to attach the at least one analyte binding molecule on the SERS-active substrate;
  c) introducing one or more analytes to the microfluidic circuit device to contact the at least one analyte binding molecule with the one or more analytes;
  d) detecting a surface enhanced Raman signal from the SERS-active substrate; and
  e) checking the obtained signal against a reference to correlate the obtained signal with the amount of the one or more analytes.

In a fourth aspect, a method for detecting haptoglobin (Hp) using surface enhanced Raman spectroscopy (SERS) is provided. The method comprises
  a) providing a biosensor according to the first aspect;
  b) introducing a first mixture comprising haemoglobin and a sample suspected to comprise haptoglobin to the microfluidic circuit device;
  c) introducing a peroxidase substrate and a peroxide source to the microfluidic circuit device and contacting with the first mixture to form a second mixture;
  d) introducing a quenching agent to the microfluidic circuit device and contacting with the second mixture to form a third mixture;
  e) contacting the third mixture with the SERS-active substrate; and
  f) detecting a surface enhanced Raman signal from the SERS-active substrate.

In a fifth aspect, a method for detecting haptoglobin (Hp) using surface enhanced Raman spectroscopy (SERS) is provided. The method comprises
  a) providing a microfluidic circuit device;
  b) introducing a first mixture comprising haemoglobin and a sample suspected to comprise haptoglobin to the microfluidic circuit device;
  c) introducing a peroxidase substrate and a peroxide source to the microfluidic circuit device and contacting with the first mixture to form a second mixture;
  d) introducing a quenching agent to the microfluidic circuit device and contacting with the second mixture to form a third mixture;

e) introducing a SERS-active substrate to the microfluidic circuit device and contacting the third mixture with the SERS-active substrate; and f) detecting a surface enhanced Raman signal from the SERS-active substrate.

BRIEF DESCRIPTION OF THE DRAWINGS

The invention will be better understood with reference to the detailed description when considered in conjunction with the non-limiting examples and the accompanying drawings, in which.

Figure 1A:
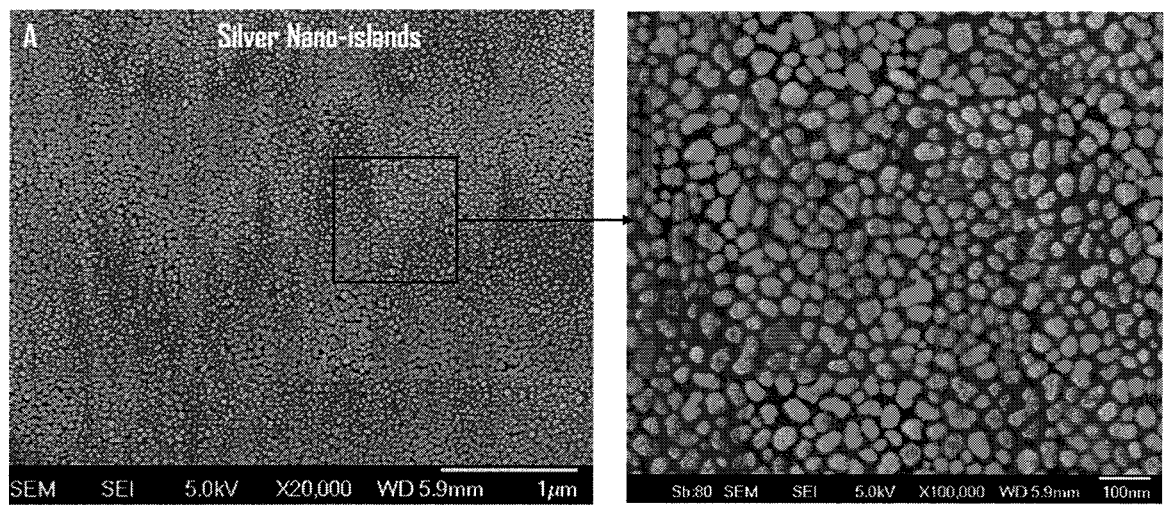
FIG. 1A is a Field Emission Scanning Electron Microscope (FESEM) image of a Silver Nano-Island (SNI) SERS substrate according to an embodiment.

The microfluidic circuit device 200 comprises an inlet region 201, which contains a first inlet 2011 and a second inlet 2012. A biological sample containing one or more analytes of interest may be introduced into the microfluidic circuit device 200 via one of the first inlet 2011 or the second inlet 2012, while a buffer medium with signal probe-tagged secondary analyte-binding molecules specific to the one or more analytes of interest may be introduced to the other inlet.

As shown, the first inlet 2011 and the second inlet 2012 are connected to a mixing region 203 via their respective microchannel 2013. As microfluidic flows have a Reynold's number that is generally low, the sample and the buffer medium may not mix readily. To facilitate the mixing, one or more mixing structures 2031 configured to induce mixing of the sample and the buffer medium may be present in the mixing region 203. For example, the one or more mixing structures 2031 may generally contain sharp bends and turns in the form of a serpentine structure to induce mixing of the sample and the buffer medium. Therefore, when analyte-containing biological samples and buffer medium with signal probe-tagged secondary analyte-binding molecules specific to the one or more analytes of interest are mixed in the mixing structures 2031, a gradient mixture with different dilution factors depending on the location of the mixing structures 2031 may be formed.

A detection region 205 may be located downstream of the mixing region 203. The detection region 205 may contain one or more reaction chambers 2051, whereby the SERS substrate disclosed herein may be comprised in or form a portion of, to allow analysis of the analyte of interest. This may, for example, be carried out through identification of the signal probe, and concentration of the analyte of interest may correspond to intensity of the signal probe.

One or more side channels 2053 are optionally present, and may be in fluid communication with the reaction chambers 2051. Various types of primary analyte-binding molecules specific for a particular analyte of interest may be introduced to the microfluidic circuit device 200 via one or more side channel inlets 2052 for immobilization into each of the side channels. In so doing, this allows multiplexing to be carried out, as multiple analytes may be detected simultaneously by virtue of analyte binding to the various types of primary analyte-binding molecule.

The mixed solution may then drained out from the microfluidic circuit device through an outlet region 207 which is in fluid communication with and located downstream of the detection region 205.

Figure 3:
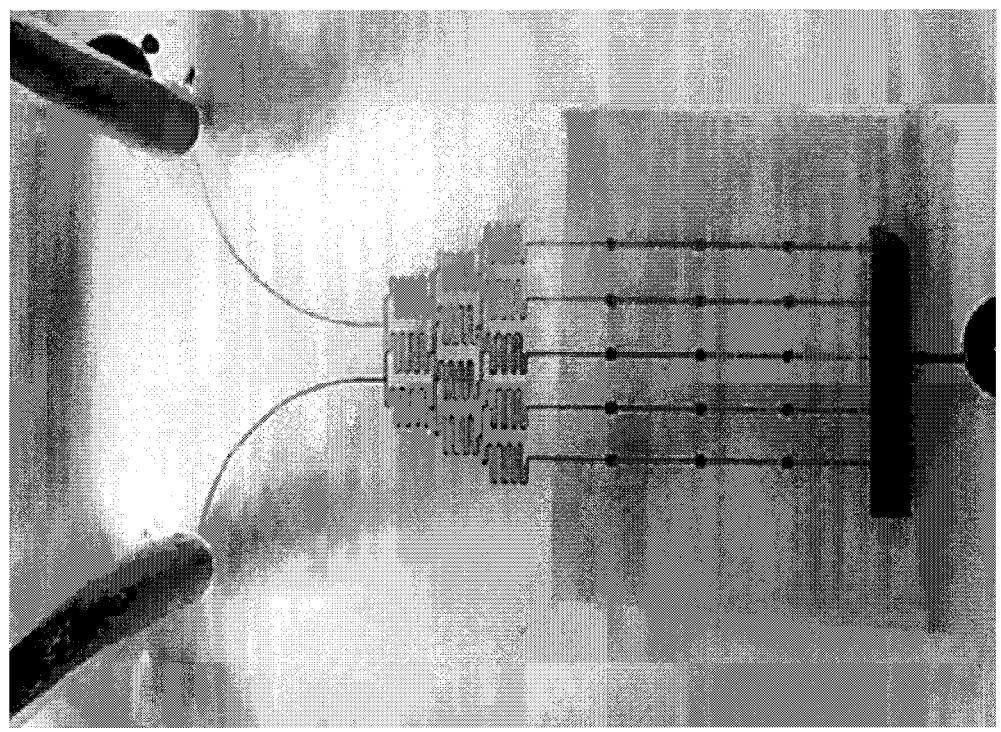
Figure 3:
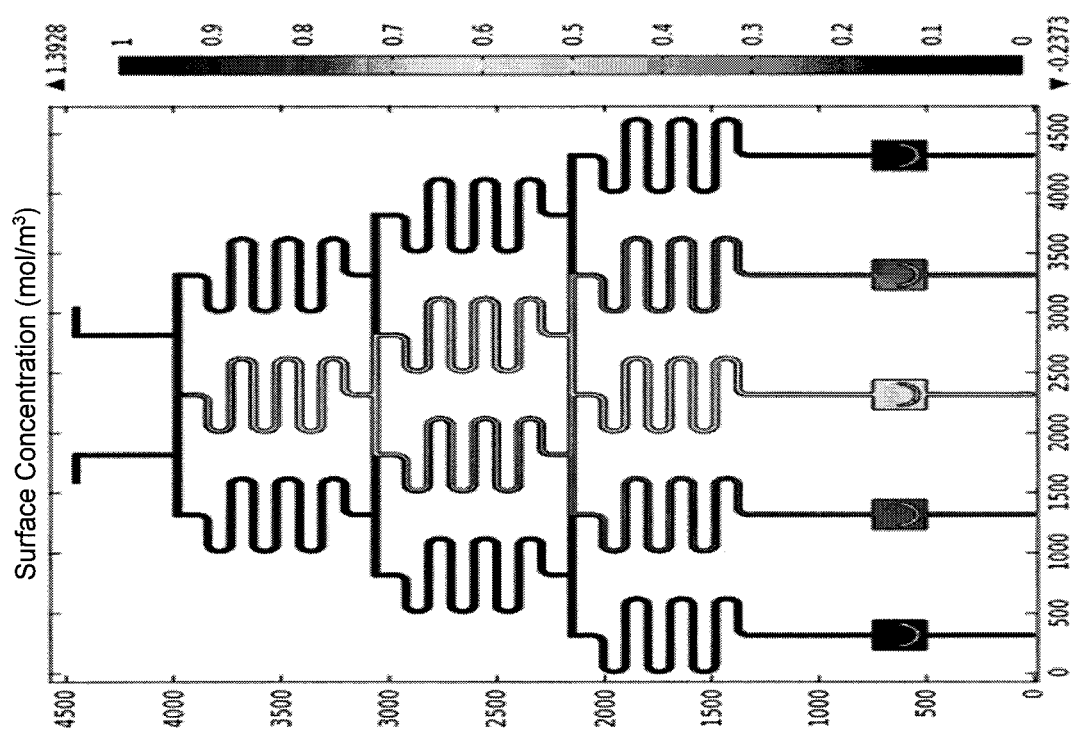

FIG. 3 depicts gradient formation inside the particular design and the as fabricated microfluidic device integrated with SERS active SNI substrate.

Figure 4A:
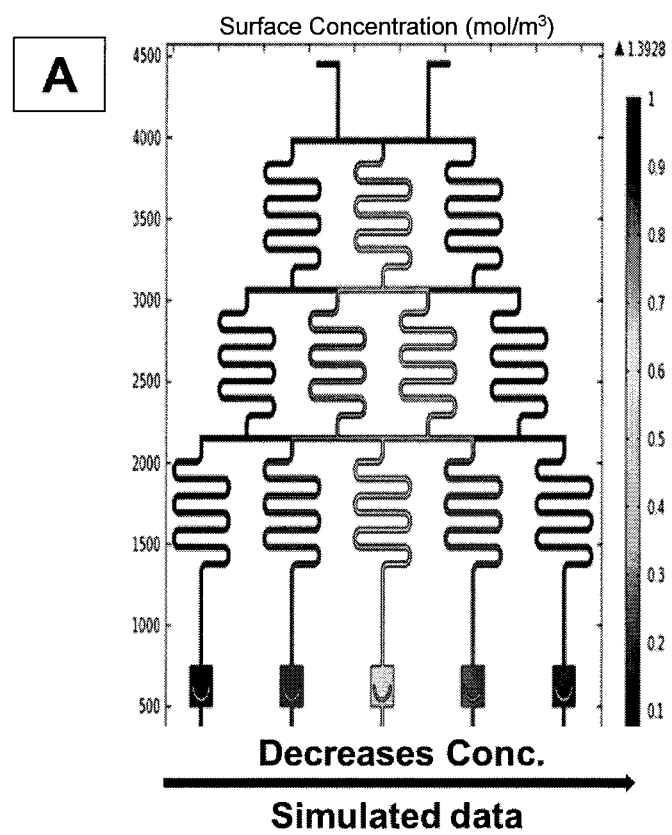

FIG. 4A is part of a proof of concept study on SERS gradient microfluidics device using 2-napthalenethiol (2-NT) SERS tag, where simulation data for gradient generation is depicted.

Figure 4B:
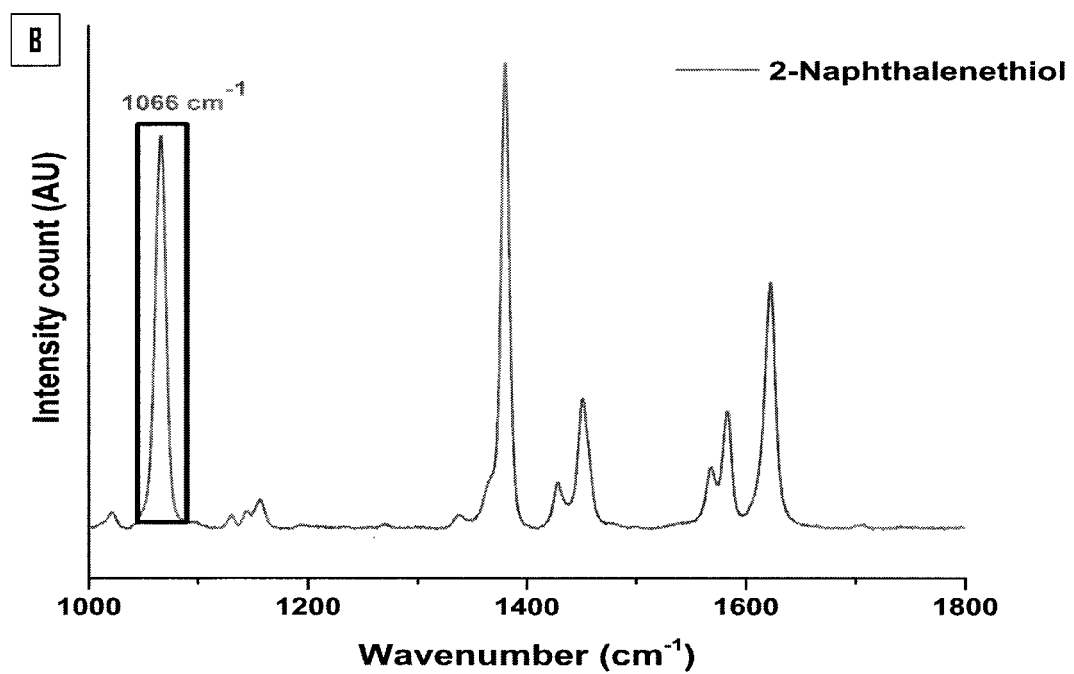

FIG. 4B is part of a proof of concept study on SERS gradient microfluidics device using 2-NT SERS tag, where SERS spectra of 2-NT with the Raman band at 1066 cm$^1$ used for concentration dependent study is shown.

Figures 4C, 4D:
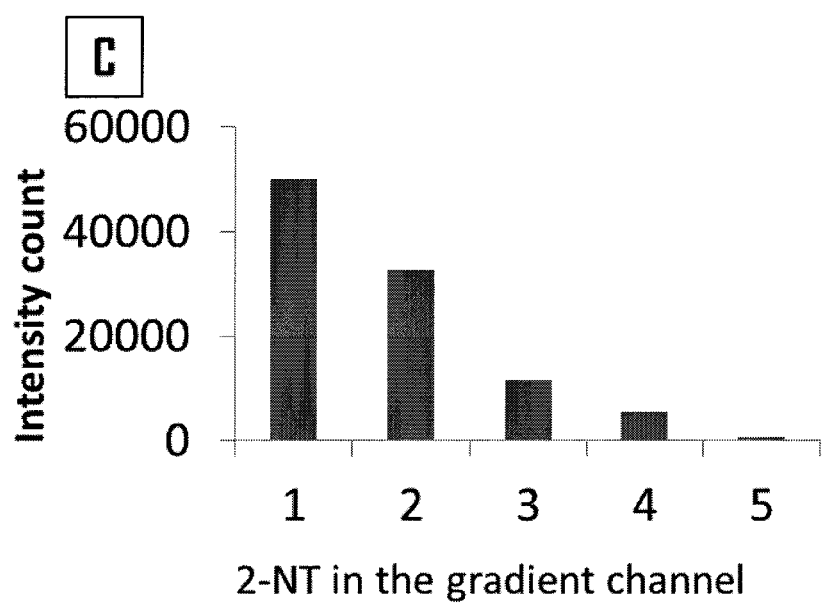

FIG. 4C is part of a proof of concept study on SERS gradient microfluidics device using 2-NT SERS tag, where plot shows concentration of 2-NT in each microchannel.

FIG. 4D is part of a proof of concept study on SERS gradient microfluidics device using 2-NT SERS tag, where table comparing the intensity count of 2-NT with that of simulated results is shown.

Figure 5:
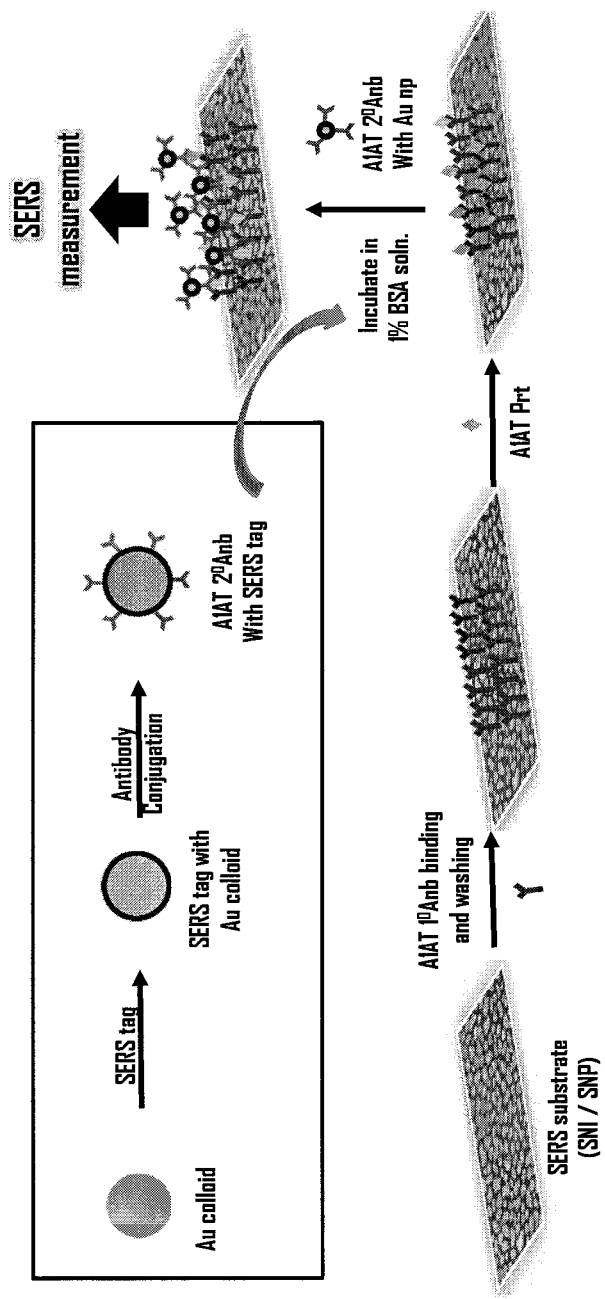

FIG. 5 is a schematic diagram for single protein detection using A1AT cancer biomarker.

Figure 6:
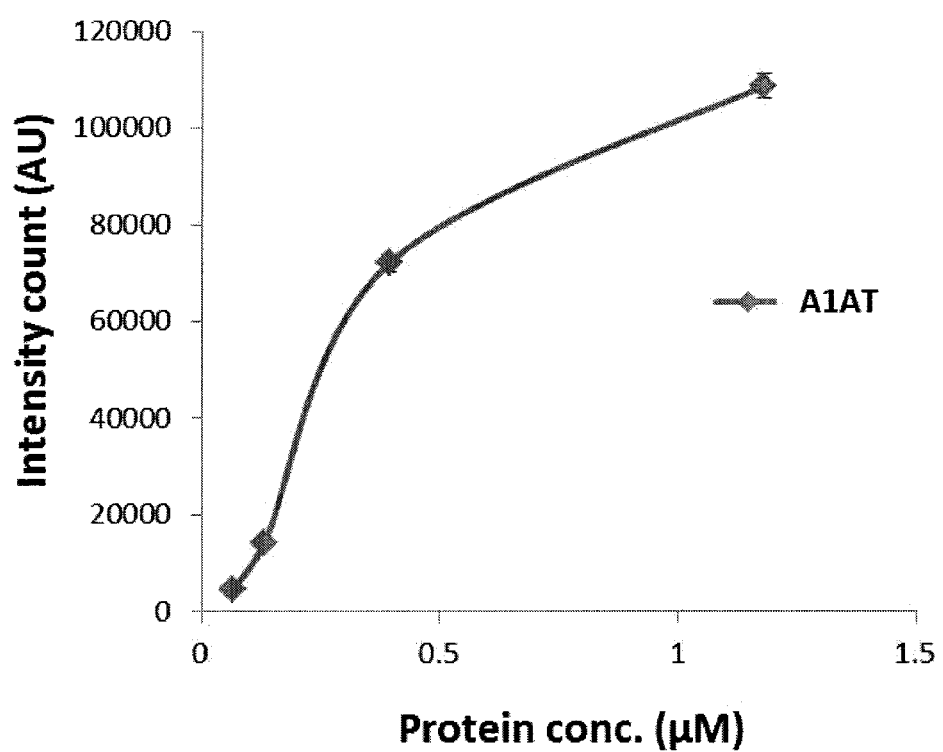

FIG. 6 is a calibration plot of A1AT protein using 4-aminothiophenol (4-ATP) SERS tag in a SNI SERS substrate based microfluidic device.

Figure 7:
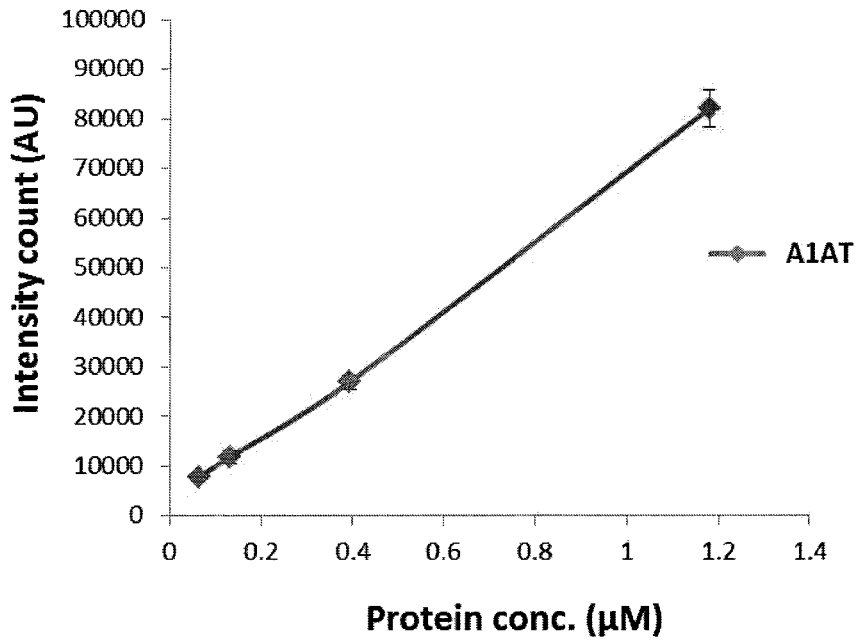

FIG. 7 is a calibration plot of A1AT protein using 4-ATP SERS tag in a SNP SERS substrate based microfluidic device.

Figure 8:
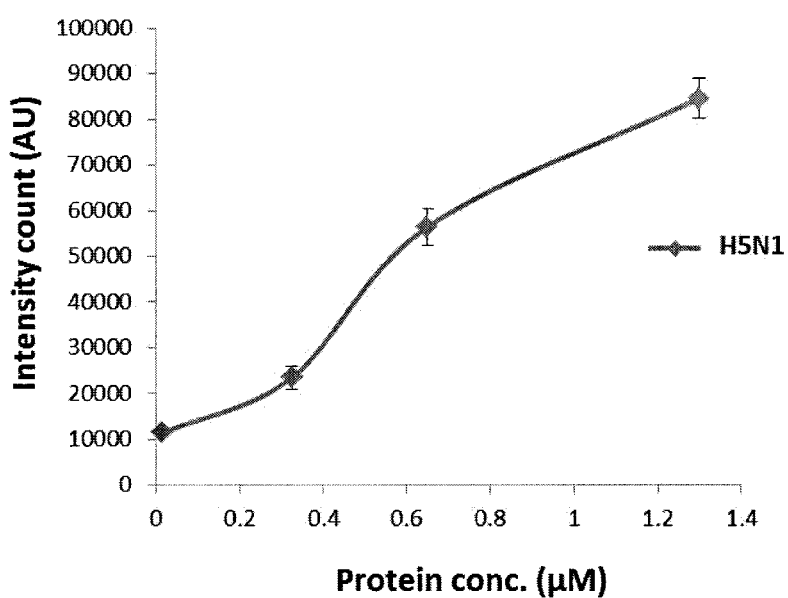

FIG. 8 is a calibration plot of H5N1 protein using 2-NT SERS tag in a SNP SERS substrate based microfluidic device.

Figure 9:
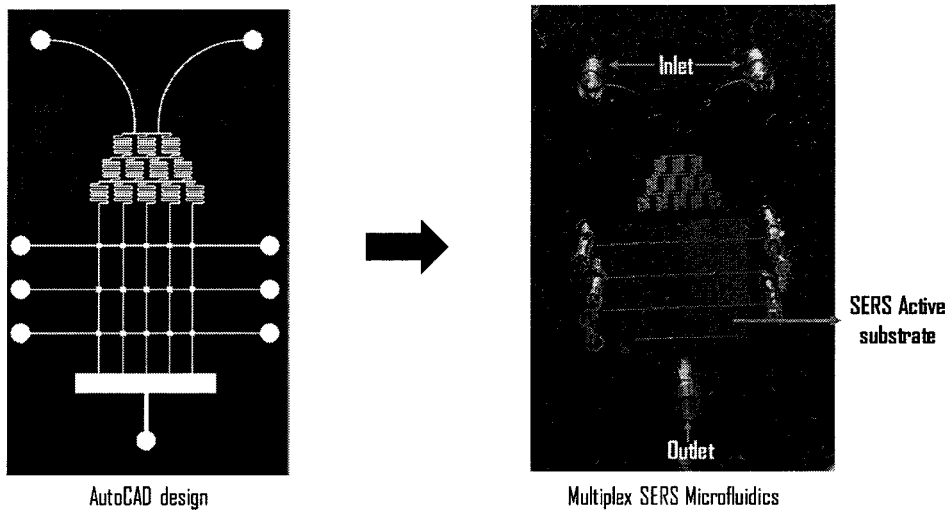

FIG. 9 shows AutoCAD design and as fabricated SERS microfluidic device with multiplexing capabilities.

Figure 10:
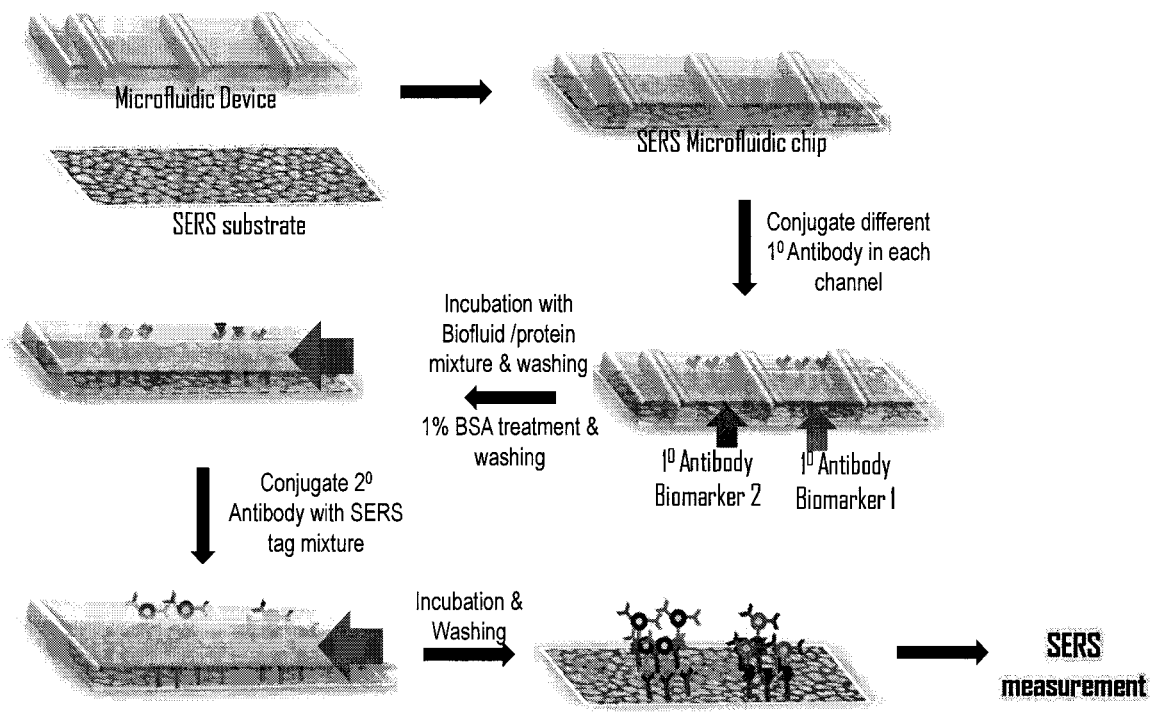

FIG. 10 is a schematic diagram depicting the multiplex biosensing mechanism using 2 infectious disease/cancer biomarkers.

Figure 11:
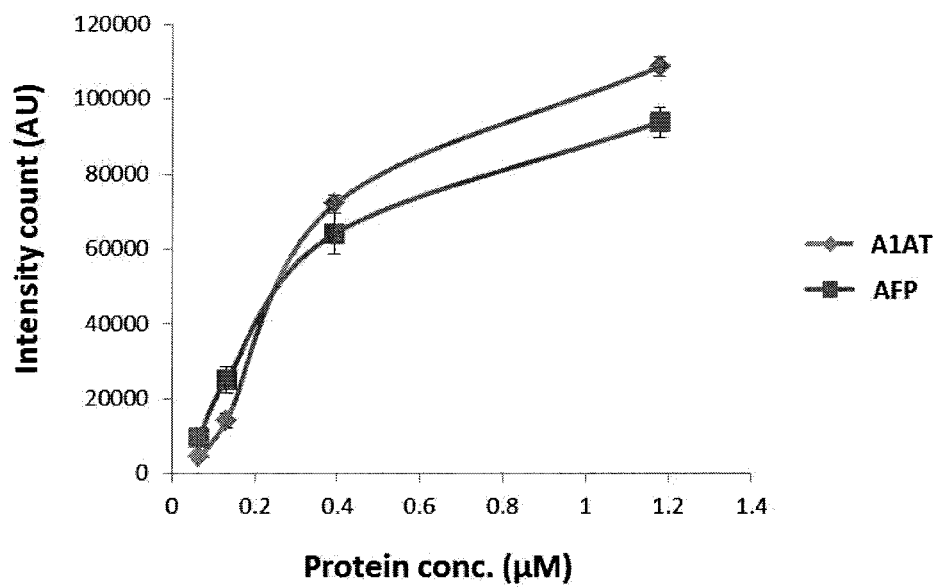

FIG. 11 is a calibration plot for the simultaneous detection and quantification of A1AT and AFP protein using 4-ATP and 4-mercaptobenzoic acid (4-MBA) SERS tags respectively.

Figure 12:
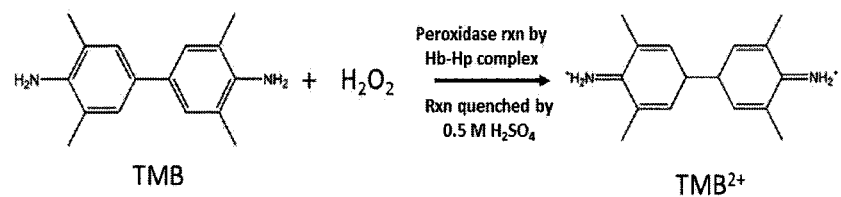

FIG. 12 shows a reaction scheme for the catalytic conversion of TMB to TMB$^{2+}$.

Figure 13:
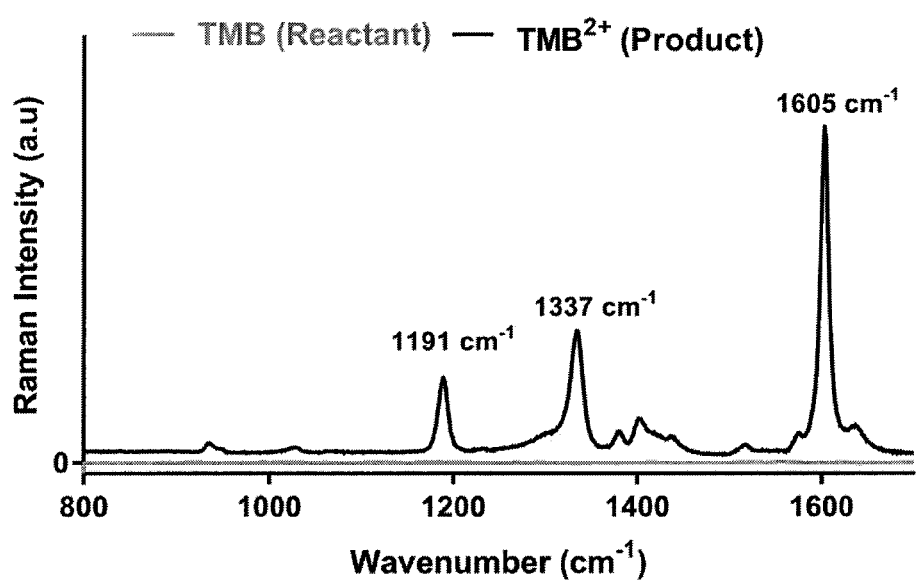

FIG. 13 is a graph showing comparison of the SERS spectra for both reactant TMB and product TMB$^{2+}$.

Figure 14:
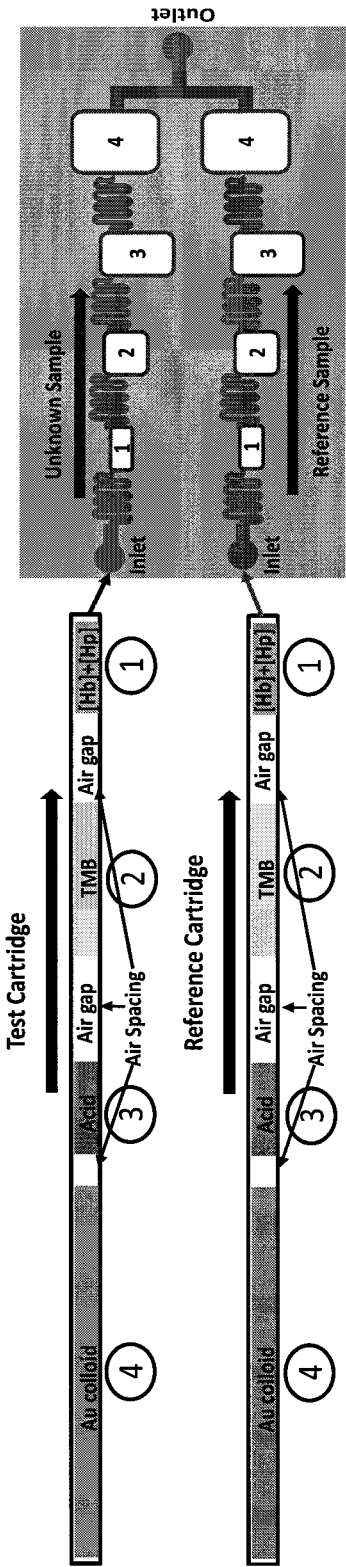

FIG. 14 is a schematic diagram showing integrated SERS microfluidic device for Haptoglobin study. Pre-loaded cartridge with reagents used for the study is shown in left and the microfluidic device with winding channel for mixing the reagents is shown on the right.

DETAILED DESCRIPTION

By integrating a SERS-active substrate with a microfluidic circuit device in the biosensor, and arranging the microfluidic circuit device to be in fluid communication with the SERS-active substrate, a novel SERS microfluidics platform which may be used to detect a single analyte, and which is capable of simultaneous multiplex detection of different analytes or biomarkers, may be obtained. Advantageously, the biosensor disclosed herein has ease of fabrication and is capable of being mass produced. In various embodiments, a SERS-active substrate with high plasmonic hot spots, and which may be reliably prepared using e-beam evaporator systems, may be used. Improved detection limits with high specificity as compared to other methodologies including colorimetric and fluorescence method may be achieved.

With the above in mind, various embodiments refer in a first aspect to a biosensor for the detection of an analyte using surface-enhanced Raman spectroscopy (SERS).

Surface-enhanced Raman spectroscopy is a form of Raman spectroscopy, which is based on an inelastic light scattering by molecules (the Raman effect). In the Raman scattering process, a photon interacts momentarily with a molecule and is then scattered into surroundings in all directions. During the brief interaction with molecule, photon loses or gains energy which is then detected and analyzed. An important aspect of the Raman scattering is the correlation between the amount of the frequency shifts and the vibrational modes of the molecules. Here, vibrational modes refer to the "manner" in which the molecule vibrates. Since vibrational modes are sensitive to the chemical nature of the molecule, probing molecular vibrations may thus reveal information regarding its chemical geometry.

In surface-enhanced Raman spectroscopy, high sensitivity may be achieved by intense enhancement of the local electromagnetic fields in the proximity of a SERS-active material such as a noble metal. Advantageously, its low water background, production of narrower spectral linewidths and no signal bleaching renders its suitability for biological samples analysis and analyte detection.

The term "detection" as used herein refers to a method of verifying the presence of a given molecule, and includes in vitro as well as in vivo detection. The detection may also be quantitative, such as correlating the detected signal with amount of analytes present.

The terms "analyte", "target molecule" or "target" as interchangeably used herein, refer to any substance that can be detected via the present method using SERS by binding to an analyte-binding molecule, and which, in some embodiments, may be present in a sample. Therefore, the analyte can be, without limitation, any substance for which there exists a naturally occurring antibody or for which an antibody can be prepared. The analyte may, for example, be an antigen, a protein, a polypeptide, a nucleic acid, a hapten, a carbohydrate, a lipid, a cell or any other of a wide variety of chemical, biological or non-biological molecules, complexes or combinations thereof.

Generally, the analyte may be a protein, peptide, carbohydrate or lipid derived from a biological source such as bacterial, fungal, viral, plant or animal samples. Additionally, however, the analyte may also be a small organic compound such as a drug, drug-metabolite, dye or other small molecule present in a sample.

A SERS-active substrate is comprised in the biosensor disclosed herein. The term "SERS-active substrate" as used herein refers to a material which is capable of enhancing Raman scattering. The SERS-active substrate may be coated with or is formed entirely of a SERS-active material, such as, but are not limited to, noble metals such as silver, palladium, gold, platinum, iridium, osmium, rhodium, ruthenium; copper, aluminum, or alloys thereof. In some embodiments, the SERS-active material is silver, gold, or alloys thereof.

For example, the SERS-active substrate may be formed from a non-SERS active material, such as plastic, ceramics, composites, glass or organic polymers, and coated with a SERS-active material such as that mentioned above to render its plasmonic characteristic. The SERS-active substrate may alternatively be formed entirely from a SERS material such as that mentioned above.

In various embodiments, the SERS-active substrate is a support comprising at least one SERS-active nanostructure disposed on a surface of the support.

The term "nanostructure" refers to a material having at least one dimension that is in the nanometer range. At least one dimension of the nanostructure may be less than 1000 nm. In various embodiments, a nanostructure has a dimension typically ranging from 100 nm to 1000 nm. Examples of a nanostructure include, but are not limited to, nano-islands, nanopillars, nanoflakes, nanoparticles, and combinations of the aforementioned.

Choice of material to form the support is not particularly limited, and may be any suitable material having a surface upon which one or more SERS-active nanostructures may e arranged.

In various embodiments, the support comprising at least one SERS-active nanostructure disposed on a surface of the support may be one of a dielectric support, a semiconductor support, or a paper support, the support comprising at least one nanostructure coated with a layer of a SERS-active material. Examples of suitable SERS-active material have already been mentioned above.

For example, the support comprising at least one SERS-active nanostructure disposed on a surface of the support may be a dielectric support, such as a glass support or a silica-coated silicon support. The at least one SERS-active nanostructure disposed on a surface of the dielectric support may be in the form of a plurality of nano-islands coated with a layer of a SERS-active material. Thickness of the layer of SERS-active material is not particularly limited, and may, in some embodiments, be in the range of about 5 nm to about 10 nm, such as about 6 nm to about 10 nm, about 8 nm to about 10 nm, about 5 nm to about 8 nm, about 5 nm to about 7 nm, or about 6 nm to about 9 nm.

As another example, the support comprising at least one SERS-active nanostructure disposed on a surface of the support may be a semiconductor support, such as a silicon support. The at least one SERS-active nanostructure disposed on a surface of the semiconductor support may be in the form of a plurality of nanopillars coated with a layer of a SERS-active material.

The plurality of nanopillars may generally have dimensions in the nanometer range. For example, the nanopillars may have a height in the range of about 250 nm to about 300 nm, such as about 270 nm to about 300 nm, about 280 nm to about 300 nm, about 250 nm to about 280 nm, about 250 nm to about 270 nm, about 260 nm to about 290 nm, or about 270 nm to about 280 nm.

Spacing between each of the nanopillars may be less than 100 nm, such as less than 90 nm, less than 80 nm, less than 70 nm, less than 50 nm, less than 30 nm, or less than. 10 nm. In some embodiments, spacing between each of the nanopillars is in the range of about 10 nm to about 100 nm, such as about 20 nm to about 100 nm, about 40 nm to about 100 nm, about 60 nm to about 100 nm, about 10 nm to about 90 nm, about 10 nm to about 70 nm, about 10 nm to about 40 nm, about 30 nm to about 80 nm.

Thickness of the layer of SERS-active material that is coated on the plurality of nanopillars is not particularly limited, and may, in some embodiments, be in the range of about 150 nm to about 250 nm, such as about 170 nm to about 250 nm, about 200 nm to about 250 nm, about 220 nm to about 250 nm, about 150 nm to about 220 nm, about 150 nm to about 200 nm, about 150 nm to about 180 nm, about 170 nm to about 230 nm, or about 180 nm to about 220 nm.

As a further example, the support comprising at least one SERS-active nanostructure disposed on a surface of the support may be a paper support, such as a chromatography paper support. The at least one SERS-active nanostructure disposed on a surface of the paper support may be in the form of a plurality of nanoparticles of a SERS-active material, such as gold and/or silver nanoparticles, which may be attached to a surface of the paper support. For example, the plurality of nanoparticles may be entrapped by fibers of the paper support, thereby being held in place on and attached to the paper support.

Size of the nanoparticles of the SERS-active material may be characterized by their diameter. The term "diameter" as used herein refers to the maximal length of a straight line segment passing through the center of a figure and terminating at the periphery. In the context of a plurality of the nanoparticles, size of the nanoparticles may be characterized by their mean diameter. The term "mean diameter" refers to an average diameter of the nanoparticles, and may be calculated by dividing sum of the diameter of each nanoparticle by the total number of nanoparticles.

In various embodiments, each of the nanoparticles of the SERS-active material has a diameter in the range of about 5 nm to about 250 nm, such as about 40 nm to about 150 nm, about 60 nm to about 100 nm, about 50 nm to about 80 nm, about 60 nm to about 80 nm, about 30 nm to about 70 nm, about 30 nm to about 60 nm, about 50 nm to about 70 nm, or about 60 nm. In specific embodiments, each of the nanoparticles of the SERS-active material has a diameter in the range of about 60 nm to about 100 nm.

The nanoparticles of the SERS-active material may be monodisperse. The term "monodisperse" refers to nanoparticles having a substantially uniform size and shape. In some embodiments, the standard deviation of diameter distribution of the nanoparticles is equal to or less than 20% of the mean diameter value, such as equal to or less than 15%, 10%, 5% or 3% of the mean diameter value. In some embodiments, the diameter of the nanoparticles of the SERS-active material is essentially the same for each nanoparticle.

In addition to or apart from the above wherein the SERS active substrate is a support comprising at least one SERS-active nanostructure disposed on a surface of the support, the SERS-active substrate may be in the form of nanoparticles of a SERS-active material. In various embodiments, the SERS-active substrate comprises or consists of gold nanoparticles. The nanoparticles of the SERS-active material mentioned above are suitable, and characteristics such as size of the nanoparticles of the SERS-active material have already been discussed above.

The biosensor disclosed herein further comprises a microfluidic circuit device arranged to be in fluid communication with the SERS-active substrate. The term "microfluidic circuit device" as used herein refers to a system or device or "chip" having a device component, such as a network of processing nodes, chambers and/or reservoirs connected by channels, which is generally fabricated at the micron or submicron scale, such as a cross-sectional dimension in the range of from about 0.1 µm to about 1000 µm.

Figure 2:
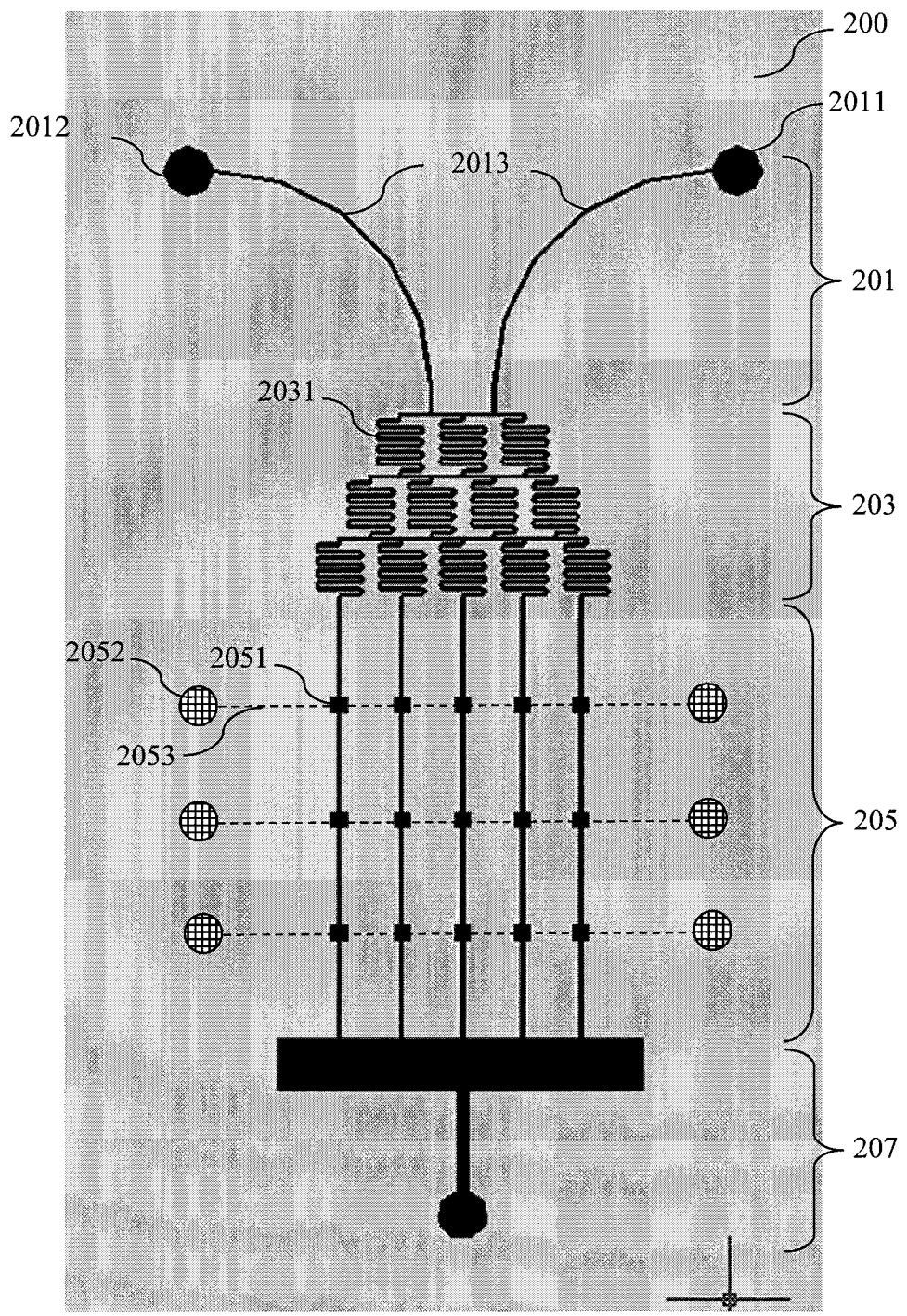
FIG. 2 is an AutoCAD drawing showing a microfluidic circuit device 200 according to an embodiment.

An example of the microfluidic circuit device according to embodiments is shown in FIG. 2.

The microfluidic circuit device may comprise two or more inlets to allow introducing (i) at least one analyte binding molecule to the microfluidic circuit device through a first inlet, and (ii) one or more analytes to the microfluidic circuit device to contact the at least one analyte binding molecule.

The at least one analyte binding molecule and the one or more analytes may be contained in a liquid reagent such as an aqueous solution, and allowed to flow into the microfluidic circuit device. As microfluidic flows have a Reynold's number that is generally low, the liquid reagents comprising the at least one analyte binding molecule and the one or more analytes may not mix readily. To facilitate the mixing, one or more mixing structures configured to induce mixing of the liquid reagents may be comprised in the microfluidic circuit device. Each of the mixing structures may, for example, contain sharp bends and turns to induce mixing.

In some embodiments, a single mixing structure is comprised in the microfluidic circuit device, and the biosensor may be used for single analyte detection.

In some embodiments, two or more mixing mixtures are comprised in the microfluidic circuit device, and the biosensor may be used for multiple analyte detection. In this regard, the mixing structures may function as a concentration gradient generator in the microfluidic circuit device. When two or more mixing structures are present in the microfluidic circuit device, for example, a gradient mixture with differing dilution factors may be generated depending on location of the two or more mixing structures. Location of the two or more mixing structures may, for example, be varied by varying flow of liquid reagent to and from the mixture structures, which may be carried out using mechanisms such as passive valves. This allows the two or more mixing structures to function as the concentration gradient generator in the microfluidic circuit device. Accordingly, the microfluidic circuit device disclosed herein may comprise a concentration gradient generator having at least two inlets and at least one outlet, and a microchannel may extend from each outlet of the concentration gradient generator. Even though two or more mixing structures are present in the microfluidic circuit device, it is also possible for the resultant biosensor to be used for single analyte detection. This may, for example, involve use of mechanisms such as passive valves to vary flow of liquid reagent in the microfluidic circuit device, such that only one mixture structure is used.

The microfluidic circuit device may be disposed on the SERS-active substrate so as to be removably attached to the SERS-active substrate, and/or may have at least a portion that is in fluid communication with the surface of the support comprising at least one SERS-active nanostructure.

As mentioned above, the microfluidic circuit device disclosed herein may comprise a concentration gradient generator. The concentration gradient generator may have at least two inlets and at least one outlet. A microchannel may extend from each outlet of the concentration gradient generator, and may define a reaction chamber. The SERS active substrate disclosed herein may be comprised in or form at least a portion of the reaction chamber. By virtue of the SERS active substrate being comprised in or forming part of the reaction chamber, this may allow the microfluidic circuit device to be in fluidic communication with the surface of the support comprising at least one SERS-active nano structure.

In various embodiments, the SERS-active substrate forms at least a portion of the reaction chamber, such as a base portion, of the microfluidic circuit device. This may be the case for embodiments wherein the SERS-active substrate is a support comprising at least one SERS-active nanostructure disposed on a surface of the support. By arranging the microfluidic circuit device on the SERS-active substrate, such that the reaction chamber of the microfluidic circuit device is arranged on/over the SERS-active substrate and is further in fluidic communication with the SERS-active substrate, for example, an interior portion of the reaction chamber may be defined by the microfluidic circuit device and the surface of the support comprising the at least one SERS-active nanostructure.

In embodiments wherein the SERS-active substrate is formed of nanoparticles of a SERS-active material, the SERS-active substrate may be comprised in the reaction chamber of the microfluidic circuit device. The nanoparticles of the SERS-active material may be introduced into the microfluidic circuit device, for example, by forming a colloidal solution comprising the nanoparticles and introducing the colloidal solution into the microfluidic circuit device via an inlet of the microfluidic circuit device.

As mentioned above, the biosensor disclosed herein is for the detection of an analyte using surface-enhanced Raman spectroscopy. To facilitate the detection, the SERS-active substrate may further comprise at least one analyte binding molecule attached thereto.

The at least one analyte-binding molecule may be one that is suitable for binding to an analyte, and may specifically bind the analyte. The phrase "specifically bind", or its grammatical variants thereof, as used herein means that the analyte-binding molecule binds to the target analyte based on recognition of a binding region on the target analyte/molecule. The analyte-binding molecule preferably recognizes and binds to the target analyte with a higher binding affinity than it binds to other compounds in the sample. Accordingly, the analyte may be attached to the SERS-active substrate via the analyte-binding molecule to allow for subsequent analysis and detection using SERS.

In various embodiments, "specifically binding" may mean that an antibody or other biological molecule, binds to a target analyte with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target analyte. Typically, specific binding refers to affinities in the range of about $10^6$-fold to about $10^9$-fold greater than non-specific binding. In some embodiments, specific binding may be characterized by affinities greater than $10^9$-fold over non-specific binding. The binding affinity may be determined by any suitable method. Such methods are known in the art and include, without limitation, surface plasmon resonance and isothermal titration calorimetry. In various embodiments, the analyte-binding molecules uniquely recognize and bind to the target analyte.

Examples of analyte-binding molecules include, but are not limited to, an antibody, antibody fragment, or antibody like molecules.

In various embodiments, the analyte-binding molecule is a proteinaceous molecule, such as an antibody, for example a monoclonal or polyclonal antibody, which immunologically binds to the target analyte at a specific determinant or epitope. The term "antibody" is used in the broadest sense and specifically covers monoclonal antibodies as well as antibody variants, fragments or antibody like molecules, such as for example, Fab, F(ab')$_2$, scFv, Fv diabodies and linear antibodies, so long as they exhibit the desired binding activity.

In various embodiments, the analyte-binding molecule is an antibody, which may be selected from the group consisting of H1N1 antibody, H5N1 antibody, A1AT antibody, AFP antibody, and combinations thereof.

To facilitate introduction of the analyte-binding molecules to the microfluidic circuit device, the microfluidic circuit device may, in some embodiments, further comprise at least one cross-flow line intersecting with and in fluid communication with each microchannel. Points at which the at least one cross-flow line and the microchannel(s) intersect may constitute intersection points that may be used to define the reaction chamber(s) of the microfluidic circuit device.

As mentioned above, the SERS active substrate disclosed herein may be comprised in or form at least a portion of the reaction chamber. Various types of analyte-binding molecules specific for a particular analyte of interest may be introduced to the microfluidic circuit device via the at least one cross-flow line, and which may be immobilized at each cross-flow line on the SERS active substrate. In so doing, this allows multiplexing to be carried out, as multiple analytes may be detected simultaneously by virtue of analyte binding to the various types of analyte-binding molecule on the SERS active substrate.

Various embodiments refer in a second aspect to a method of manufacturing a biosensor for the detection of an analyte using surface-enhanced Raman spectroscopy (SERS) according to the first aspect. The method may comprise providing a SERS-active substrate, and arranging a microfluidic circuit device to be in fluid communication with the SERS-active substrate to obtain the biosensor.

As mentioned above, the SERS-active substrate may be in the form of a support comprising at least one SERS-active nanostructure disposed on a surface of the support. Accordingly, providing the SERS-active substrate may comprise providing a support and forming at least one SERS-active nanostructure on a surface of the support.

In various embodiments, the support comprising at least one SERS-active nanostructure disposed on a surface of the support may be one of a dielectric support, a semiconductor support, or a paper support, the support comprising at least one nanostructure coated with a layer of a SERS-active material. Examples of suitable SERS-active material have already been mentioned above.

In some embodiments, the support is a dielectric support. Providing a support and forming at least one SERS-active nanostructure on a surface of the support may accordingly comprise providing a dielectric support. At least one nanostructure may be formed on a surface of the dielectric support. Forming the at least one nanostructure on a surface of the support may be carried out by electron-beam evaporation. In some embodiments, the electron-beam evaporation is carried out at a pressure in the range of about $10^{-6}$ mbar to about $10^{-7}$ mbar.

Figure 1B:
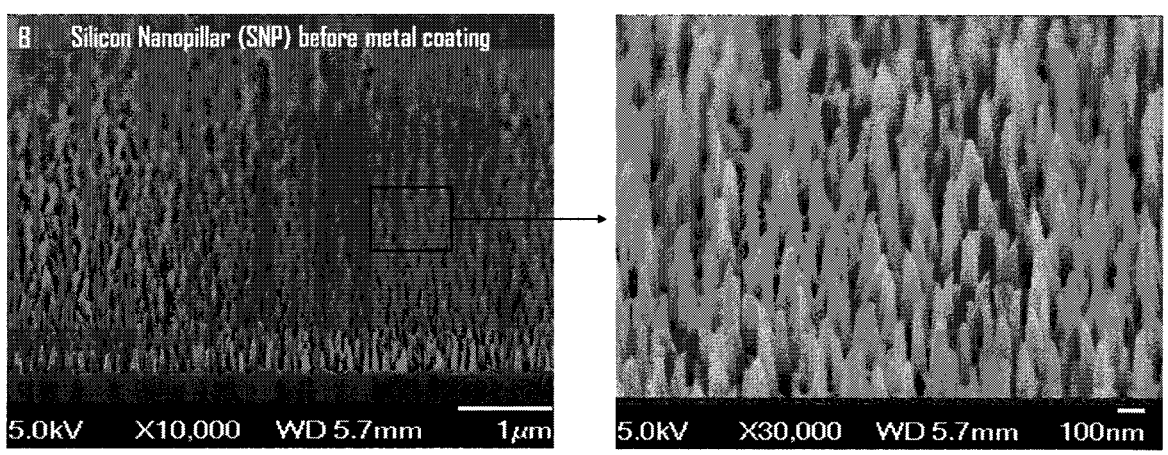
FIG. 1B is a Field Emission Scanning Electron Microscope (FESEM) image of a Silicon Nanopillar (SNP) SERS substrate (before metal coating) according to an embodiment.
Figure 1C:
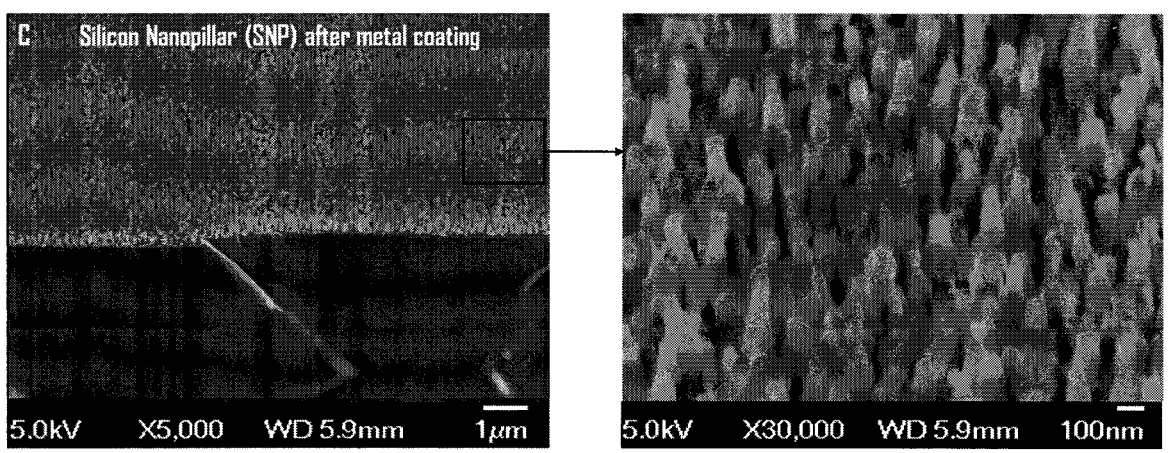
FIG. 1C is a Field Emission Scanning Electron Microscope (FESEM) image of the Silicon Nanopillar (SNP) SERS substrate of FIG. 1B after metal coating according to an embodiment.

A layer of a SERS-active material, such as silver and/or gold, is formed on the at least one nanostructure, which may be formed using any suitable technique such as sputtering or E-beam evaporation method. For example, E-beam evaporation of silver to a thickness of around 7 nm was used to obtain randomly arranged sporadic nanoparticles as shown in FIG. 1A. As a further example, sputtering method was used to coat thin silver film over silicon nanopillar structures as shown in FIG. 1C.

In various embodiments, the layer of SERS-active material is deposited at an evaporation rate in the range of about 0.01 nm/s to about 0.1 nm/s, such as about 0.03 nm/s to about 0.1 nm/s, about 0.05 nm/s to about 0.1 nm/s, about 0.07 nm/s to about 0.1 nm/s, about 0.01 nm/s to about 0.08 nm/s, about 0.01 nm/s to about 0.05 nm/s, or about 0.03 nm/s to about 0.8 nm/s.

In some embodiments, the support is a semiconductor support. Providing a support and forming at least one SERS-active nanostructure on a surface of the support may accordingly comprise providing a semiconductor support. At least one nanostructure may be formed on a surface of the semiconductor support by inductively-coupled plasma reactive ion etch.

The inductively-coupled plasma reactive ion etch may comprise subjecting the semiconductor support to an oxygen plasma treatment carried out at a pressure in the range of about 10 mTorr to about 15 mTorr, such as about 12 mTorr to about 15 mTorr, or about 10 mTorr to about 13 mTorr, which may be carried out for a time period in the range of about 5 minutes to about 10 minutes. The resultant semiconductor support may be etched using a combination of $SF_6:O_2$ gas having a ratio in the range of about 1.1 to about 1.21 at an etch rate in the range of about 2.5 nm/s to about 2.8 nm/s, such as about 2.6 nm/s to about 2.8 nm/s, or about 2.5 nm/s to about 2.7 nm/s.

A layer of a SERS-active material, such as silver and/or gold, may be formed on the at least one nanostructure, and which may be carried out by at least one of e-beam deposition or sputtering.

In some embodiments, the support is a paper support. Providing a support and forming at least one SERS-active nanostructure on a surface of the support may accordingly comprise providing a paper support, such as a chromatography paper support, and attaching a plurality of silver and/or gold nanoparticles to a surface of the paper support. Attaching the plurality of silver and/or gold nanoparticles to a surface of the paper support may be carried out by at least one of e-beam vapor deposition, sputtering, or syringe filtration.

In addition to or apart from the above, the SERS-active substrate may be in the form of nanoparticles of a SERS-active material, such as gold nanoparticles. Providing a SERS-active substrate may accordingly comprise forming the nanoparticles.

To obtain the biosensor, a microfluidic circuit device is arranged to be in fluid communication with the SERS-active substrate.

The microfluidic circuit device disclosed herein may be fabricated using traditional machining techniques such as microinjection molding and computerized numerically controlled (CNC) machining, or precision injection molding, as can be understood by persons skilled in the art. In some embodiments, the microfluidic circuit device is fabricated using precision injection molding, and may be formed from a polymer such as polydimethylsiloxane (PDMS), polycarbonate, poly(methyl methacrylate) (PMMA), copolymers thereof, and combinations thereof.

The interior surfaces of the microfluidic circuit device, including device components such as processing nodes, chambers, reservoirs, and/or channels, may be cleaned or sterilized where required. In some cases, the inner surfaces of the chambers and channels may be coated with another material so as to modify the surface properties of the surfaces.

In various embodiments, the method disclosed herein may further comprise subjecting the SERS-active substrate and the microfluidic circuit device to an oxygen plasma treatment prior to arranging the microfluidic circuit device to be in fluid communication with the SERS-active substrate. The oxygen plasma may be carried out to create oxygen free radicals on the SERS-active substrate and the microfluidic circuit device, so as to facilitate leak free bonding of the two structures.

In addition or alternatively, the SERS-active substrate and the microfluidic circuit device may be heat treated at a temperature in the range of about 80° C. to about 150° C., such as about 100° C. to about 150° C., about 120° C. to about 150° C., about 80° C. to about 120° C., or about 80° C. to about 100° C. after arranging the microfluidic circuit device to be in fluid communication with the SERS-active substrate. As in the case for oxygen plasma treatment mentioned above, the heat treating may be carried out to facilitate bonding such as crosslinking between the SERS-active substrate and the microfluidic circuit device. The heat treatment may be carried out for a time period in the range of about 30 minutes to about 90 minutes, for example, about 40 minutes to about 90 minutes, about 60 minutes to about 90 minutes, about 30 minutes to about 70 minutes, or about 50 minutes to about 70 minutes.

Various embodiments refer in a third aspect to a method for detecting at least one analyte using surface enhanced Raman spectroscopy (SERS).

As mentioned above, in surface-enhanced Raman spectroscopy, high sensitivity may be achieved by intense enhancement of the local electromagnetic fields in the proximity of a SERS-active material, where the Raman signal generated may be enhanced by several orders of magnitude due to the strong surface plasmon resonance. Therefore, methods disclosed herein has higher sensitivity as compared to state of the art methods such as ELISA. Advantageously, multiple steps in ELISA required to achieve the same result as that of the SERS microfluidics disclosed herein are also avoided.

The method comprises providing a biosensor according to the first aspect, and introducing at least one analyte binding molecule to the microfluidic circuit device to attach the at least one analyte binding molecule on the SERS-active substrate. The at least one analyte binding molecule may be introduced to the microfluidic circuit device via an inlet of the microfluidic circuit device.

Examples of suitable analyte binding molecule have already been mentioned above. In various embodiments, the at least one analyte binding molecule specifically binds the one or more analytes, and may be selected from the group consisting of an antibody such as H1N1 antibody or H5N1 antibody, antibody fragment or antibody like molecules.

In some embodiments, the at least one analyte binding molecule is attached to a surface of the SERS-active substrate via a linker molecule, which refers to molecules having one or more functional groups that can bind or link the at least one analyte binding molecule to the SERS-active substrate. The functional group(s) on the linker molecules may allow covalent bonding of the at least one analyte binding molecule to the SERS-active substrate to prevent their dislodgement, thereby resulting in mechanical stability of the at least one analyte binding molecule on the SERS-active substrate. Generally, any functional group is able to bind the analyte binding molecule to the surface of the SERS-active substrate may be used. Examples of functional groups include, but are not limited to, a thiol group, an amino group, and a carboxy group. Type of linker molecules that are suitable for use may depend on the analyte binding molecule and the SERS-active substrate. In some embodiments, the linker molecule is thiolated PEG with carboxylic acid functional group.

One or more analytes may be introduced to the microfluidic circuit device to contact the at least one analyte binding molecule with the one or more analytes. Examples of suitable analytes have already been discussed above. In various embodiments, the one or more analytes may be selected from the group consisting of proteins such as alpha-1 antitrypsin (A1AT) and alpha-fetoprotein (AFP), peptides, nucleic acids, carbohydrates, lipids, cells, viruses, small molecules, and combinations thereof.

The one or more analytes may, for example, be contained in a sample, meaning that the detection is in vitro.

The term "sample", as used herein, refers to an aliquot of material, frequently biological matrices, an aqueous solution or an aqueous suspension derived from biological material. The samples used may vary based on the assay format and the nature of the tissues, cells, extracts or other materials, especially biological materials, to be assayed.

Non-limiting examples of samples include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed.

A further SERS-active substrate may be introduced to the microfluidic circuit device after the one or more analytes are introduced. The further SERS-active substrate may comprise a further analyte binding molecule, a Raman-active marker compound and a metallic nanoparticle, wherein the further analyte binding molecule and the Raman-active marker compound are independently covalently attached to the metallic nanoparticle.

The metallic nanoparticle may be coated with or consists of a metal selected from the group consisting of a noble metal, such as gold and/or silver, copper, aluminum, and alloys thereof.

As used herein, the term "Raman-active marker compound" refers to a compound which has a high Raman cross section. In various embodiments, the Raman-active marker compound is selected from the group consisting of 4-aminothiophenol (4-ATP), 2-napthalenethiol (2-NT), 4-methylbenzenethiol, rhodamine B isothiocyanate, methylene blue, coumarin, melamine, and combinations thereof.

The further analyte binding molecule may be the same as or different from the analyte binding molecule mentioned above. In embodiments wherein the analyte binding molecule and the further analyte binding molecule are antibodies, for example, the analyte binding molecule may be termed a primary antibody, while the further analyte binding molecule may be termed a secondary antibody.

As in the case for the analyte binding molecule, the further analyte binding molecule may specifically bind to the analyte that is bound on the analyte binding molecule that is attached on the SERS-active substrate. Since the further analyte binding molecule is covalently attached to the metallic nanoparticle, which also has a Raman-active marker compound covalently attached thereto, detecting a surface enhanced Raman signal from the SERS-active substrate allows determination of presence and/or amount of analyte that is present. In the context of the primary and secondary antibodies mentioned above, for example, the primary antibody may be used to capture the analyte of interest, while the secondary antibody, by virtue of it specifically binding to the analyte, may be used to associate the signal probe present on the metallic nanoparticle with the analyte.

Accordingly, a surface enhanced Raman signal may be detected from the SERS-active substrate; and the obtained signal may be checked against a reference to correlate the obtained signal with the amount of the one or more analytes.

In various embodiments, the reference is generated using a microfluidic circuit device comprising a concentration gradient generator such as that mentioned above and expresses intensity of SERS signal as a function of analyte concentration. In this regard, the reference may be in the form of a calibration plot of intensity count against analyte concentration, which may be specific to the Raman-active marker compound used, to allow derivation of the analyte concentration by interpolating the SERS intensity count of the unknown samples.

Advantageously, the method disclosed herein may be a multiplex method for detecting more than one analyte, such as two or more different analytes. This usually requires the use of more than one type of analyte-binding molecule in the contacting step so that each analyte is bound by a specific type of analyte-binding molecule. For example, two or more different types of analyte-binding molecule may be attached or immobilized on SERS active substrate in different parts, such as different reaction chambers, of the microfluidic circuit device. This allows binding of different target analytes to the different types of analyte-binding molecule. By detecting a surface enhanced Raman signal from each of the individual reaction chambers, detection of the two or more different types of analyte-binding molecule may be carried out.

As mentioned above, analytes which may be detected using a biosensor disclosed herein may include, but are not limited to, proteins, entities associated with cause of diseases such as cancer, or any other biomolecules. One example of an analyte which may be detected is Haptoglobin (Hp). Haptoglobin belongs to a family of acute phase serum glycoproteins. It may be mostly generated by hepatocytes in the liver and in little amounts by skin, kidneys and the lungs. Under normal conditions, it may be either absent or present at very low levels. However, Hp may increase significantly in response to acute infection, inflammation or trauma. Recent studies have shown that Hp may be elevated in the sera and ascetic fluid of pre-operative ovarian cancer patients and a decrease was observed in patients undergoing chemotherapy. Therefore, enhanced sensitivity, improved analysis and quantification reliability with faster detection of acute phase protein and ovarian cancer biomarker Hp are of interest.

Various embodiments refer accordingly in a further aspect to a method for detecting haptoglobin (Hp) using surface enhanced Raman spectroscopy (SERS).

In exemplary embodiments, the analyte is haptoglobin (Hp), while the analyte-binding molecule is haemoglobin (Hb). SERS may be employed to detect and quantify Hp based on the peroxidase activity of [Hp-Hb] complex to catalyze the reaction of a peroxidase substrate such as TMB and a peroxide source such as $H_2O_2$. By contacting haemoglobin with a sample suspected to comprise haptoglobin under conditions that allow formation of a haptoglobin-haemoglobin [Hp-Hb] complex to form a first mixture, and contacting a peroxidase substrate and a peroxide source with the resultant mixture, along with addition of a quenching agent and a SERS-active substrate, a surface enhanced Raman signal may be detected from a surface of the SERS-active substrate to allow detection of the haptoglobin.

A principle behind this reaction may be that free haemoglobin (Hb) which exhibits peroxidase activity, is likely to be inhibited at a low pH. Hp present in the specimen or a test sample combines with Hb, and at a low pH preserves the peroxidase activity of the bound Hb. Preservation of the peroxidase activity of Hb may be directly proportional to the amount of Hp present. Hence, the peroxidase active [Hb-Hp]

complex may oxidize a SERS inactive chromogenic reactant, such as but not limited to, 3,3',5,5'-Tetramethyl benzidine (TMB) (e.g. in the form of a liquid), into a SERS-active product $TMB^{2+}$.

Accordingly, the method disclosed herein may allow a more robust and efficient detection of the analyte, while providing higher sensitivity in detection as compared to traditional chromogenic tests.

The method may comprise providing a biosensor disclosed herein, and introducing a first mixture comprising haemoglobin and a sample suspected to comprise haptoglobin to the microfluidic circuit device.

A peroxidase substrate and a peroxide source may be introduced to the microfluidic circuit device and contacted with the first mixture to form a second mixture.

The peroxidase substrate may be selected from the group consisting of 3,3',5,5'-tetramethylbenzidine, horseradish peroxidase, o-phenylenediamine, biphenyl-4,4'-dithiol, 5-bromo-4-chloro-3-indolyl phosphate, 2,2'-azino-bis(3-ethylbenzthiazoline-6-sulfonic acid), and combinations thereof. In some instances, the peroxidase substrate may be selected from the group consisting of 3,3',5,5'-tetramethylbenzidine, o-phenylenediamine, biphenyl-4,4'-dithiol, 5-bromo-4-chloro-3-indolyl phosphate, 2,2'-azino-bis(3-ethylbenzthiazoline-6-sulfonic acid), or combinations thereof. Advantageously, these peroxidase substrates, particularly 3,3',5,5'-tetramethylbenzidine, are non-toxic, which compares favorably with substrates such as o-phenylenediamine, biphenyl-4,4'-dithiol, and 5-bromo-4-chloro-3-indolyl phosphate which are toxic.

The peroxide source may be selected from the group consisting of hydrogen peroxide, carbamide peroxide, sodium perborate, sodium percarbonate, urea peroxide, and combinations thereof. Other peroxide sources which may be capable of releasing peroxide upon contact with an aqueous solvent, e.g. water, may be used. The peroxide source may comprise or consist of hydrogen peroxide.

The second mixture may be quenched by introducing a quenching agent, such as a strong acid, a free haemoglobin inhibitor, a protein binding inhibitor, a peroxide-reducing enzyme, or combinations thereof, to the microfluidic circuit device and contacting with the second mixture to form a third mixture.

The third mixture may be contacted with the SERS-active substrate; and a surface enhanced Raman signal may be detected from the SERS-active substrate.

In various embodiments, the first mixture, the peroxidase substrate, the peroxide source, and the quenching agent are comprised in a cartridge with each being spaced apart by an air gap. The first mixture, the peroxidase substrate, the peroxide source, and the quenching agent may, for example, be comprised in a cartridge and arranged in order based on their addition sequence to the microfluidic circuit device. Advantageously, this may reduce the multistep reaction into a single step to allow performing of the reaction on a microfluidic platform.

Various embodiments refer in a further aspect to a method for detecting haptoglobin (Hp) using surface enhanced Raman spectroscopy (SERS). The method may comprise providing a microfluidic circuit device, to which a first mixture comprising haemoglobin and a sample suspected to comprise haptoglobin may be introduced.

A peroxidase substrate and a peroxide source may be introduced to the microfluidic circuit device and contacted with the first mixture to form a second mixture. Examples of suitable peroxidase substrate and peroxide source have already been discussed above.

The second mixture may be quenched by contacting with a quenching agent, which may be introduced to the microfluidic circuit device. In embodiments wherein a quenching agent is used, the quenching agent may form a third mixture with the second mixture.

A SERS-active substrate, such as nanoparticles of a SERS-active material, may be introduced to the microfluidic circuit device and the third mixture may be contacted with the SERS-active substrate, from which a surface enhanced Raman signal may be detected.

In various embodiments, the first mixture, the peroxidase substrate, the peroxide source, and the quenching agent are comprised in a cartridge with each being spaced apart by an air gap. The first mixture, the peroxidase substrate, the peroxide source, the quenching agent, and the SERS-active substrate may be comprised in a cartridge and arranged in order based on their addition sequence to the microfluidic circuit device. Advantageously, this may reduce the multistep reaction into a single step to allow performing of the reaction on a microfluidic platform.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Various embodiments disclosed herein relate to fabrication of simple and cost effective SERS based microfluidic bio-sensing platform with multiplexing capability as a point of care diagnostic system for the biomarker detection and quantification.

Various SERS substrates may be used, such as that detailed in the following publications which provide protocols for the fabrication of reliable SERS substrate.

1. J. Perumal, K. V. Kong, U. S. Dinish, R. M. Bakker and M. Olivo, RSC Adv., 2014, 4(25), 12995-13000;

2. Z. X. Genga, W. Liu, X. D. Wang, F. H. Yang, Sensors and Actuators A, 2011, 169, 37-42;

3. B. B. Xu, Z. C. Ma, H. Wang, X. Q. Liu, Y. L. Zhang, X. L. Zhang, R. Zhang, H. B. Jiang and H. B. Sun, Electrophoresis, 2011, 32, 3378-3384;

4. D. Kim, A. R. Campos, A. Datt, Z. Gao, M. Rycenga, N. D. Burrows, N. G. Greeneltch, C. A. Mirkin, C. J. Murphy, R. P. Van Duyne, C. L. Haynes, Analyst, 2014, 139, 3227; and 5. K. R. Ackermann, T. Henkel and J. Popp, ChemPhysChem, 2007, 8, 2665-2670.

Three different SERS substrate platforms according to embodiments were used to illustrate the concept.

One of the SERS active substrate is a Silver Nano-Islands (SNI) that can be directly fabricated onto the dielectric substrate such as glass, SiO2 coated Si wafer and integrated into the polymer microfluidic device. In addition to this, the inventors have used advanced Silicon Nanopillar (SNP) substrate fabricated by means of Silicon blanket etch method using $SF_6$ and $O_2$ gases. The inventors have also used SNP as SERS active substrate and integrated them with microfluidic device. Paper based SERS substrates were also explored for biosensing study.

The microfluidic design according to an embodiment includes two inlet gradient microchannel with serpentine design to enhance the mixing efficiency between the buffer and the sample. The gradient microchannel design may assist in finding the highest and lowest detectable concentration in parallel. Microfluidic biosensor performance may be analyzed by studying reproducibility and signal enhancement from the Raman active molecule, 2-naphthalenethiol (NT) which is covalently anchored to the substrate.

As a continuation, SNI and SNP based microfluidics were used for detection of disease and cancer biomarkers. For this study, different SERS tags with 4-aminothiophenol (4-ATP) & 2-NT were used as Raman active molecule. In single protein detection, the inventors detected A1AT & H5N1 which are cancer and infectious disease biomarkers respectively. This SERS microfluidic device is also capable of performing simultaneous detection of biomarkers for disease/cancer and other metabolic disorders in a multiplexing approach using different microfluidic designs. As a proof, the inventors have simultaneously detected 2 cancer biomarkers using sandwich biosensing approach.

Example 1: Preparation of Silver Nano-Island (SNI) SERS Substrate Samples

Silver Nano-Island (SNI) SERS substrate samples were fabricated for the experiments using electron-beam evaporation system, which involves a physical vapor deposition technique. Any dielectric substrates may be used. In the experiments carried out, either borosilicate glass or silica coated silicon wafers were placed in an electron-beam vacuum evaporation chamber. The pressure inside the chamber was maintained at $10^{-6}$ to $10^{-7}$ millibar during the deposition process. The inventors then deposited 7 nm thick layer of silver using an evaporation rate of approximately 0.05 nm/s. Thickness of the film and deposition rate were monitored with a quartz crystal oscillator. FESEM image of the SNI sample is shown in FIG. 1A.

Example 2: Preparation of Silicon Nanopillar (SNP) SERS Substrate Samples

For fabrication of Silicon Nanopillar (SNP) SERS substrate samples, silicon etch was performed using Inductively-Coupled Plasma Reactive Ion Etch system (ICP-RIE) from Oxford Instruments. Undoped or P type silicon wafer may be used for SNP fabrication.

As a first step, the Si wafer was subjected to oxygen plasma treatment using $O_2$ gas under $10^{-15}$ mTorr chamber pressure for 5 min to 10 min based on the requirement. This step was carried out in order to increase the oxidized silica layer on the silicon surface.

In the second step, a combination of $SF_6$:$O_2$ gas was used in a ratio of 1.1 to 1.21 at the etch rate of 2.5 to 2.8 nm/s. Randomly arranged Si nanopillars with 250 to 300 nm height were obtained, and spacing between the nanopillar was below 100 nm. FIG. 1B shows FESEM image of bare SNP.

Following this step, either silver only, or a combination of silver and gold may be deposited by means of e-beam evaporation or sputtering process. FIG. 1C shows FESEM image of SNP after depositing 200 nm silver by e-beam deposition process. The resultant SNP was ready and used for subsequent SERS study.

Example 3: Preparation of Paper SERS Substrate Samples

Figure 1D:
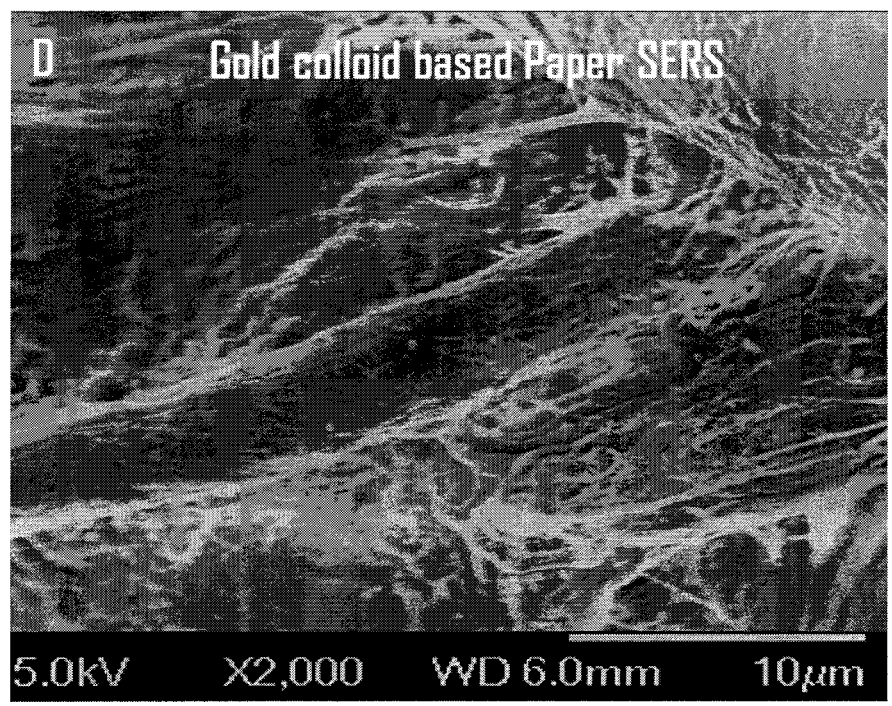
FIG. 1D is a Field Emission Scanning Electron Microscope (FESEM) image of a paper SERS substrate with gold (Au) colloid according to an embodiment.
Figure 1E:
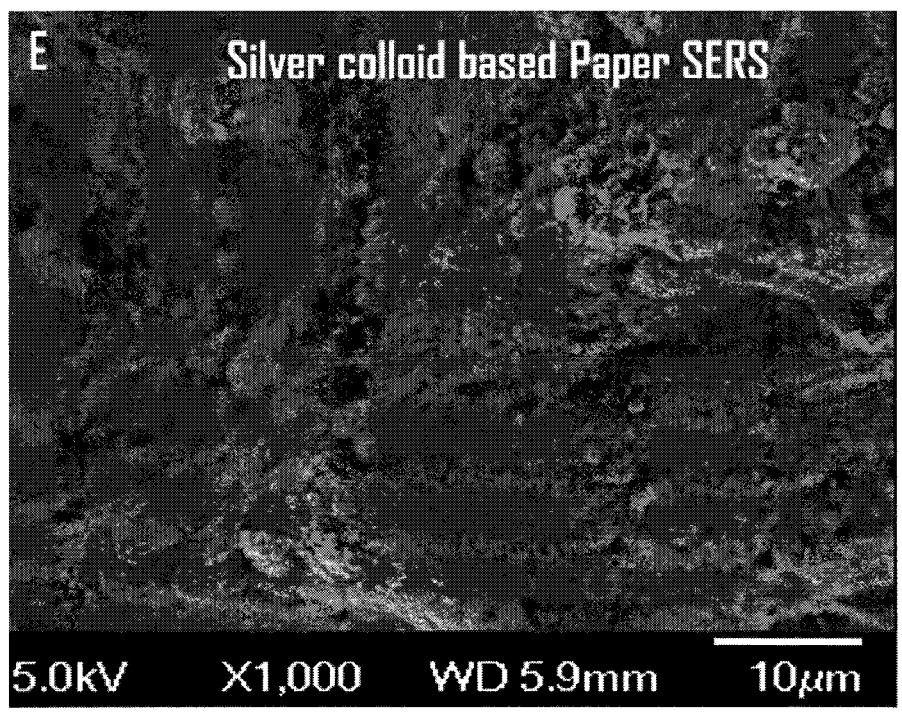
FIG. 1E is a Field Emission Scanning Electron Microscope (FESEM) image of a paper SERS substrate with silver (Ag) colloid according to an embodiment.

As a third alternative for SERS substrate, the inventors also explored the use of paper SERS. For the fabrication process, Whatman chromatographic paper (from Sigma-Aldrich) was used. The inventors adopted two methods, first method by e-beam vapor deposition/sputtering, and second method using syringe filter to infiltrate Ag/Au colloidal nanoparticles into the Chromatographic paper. FIG. 1D and FIG. 1E show the paper SERS substrate with both Au colloid and Ag colloid respectively.

Example 4: Fabrication of Polydimethylsiloxane (PDMS) Based Microfluidic Device

A gradient microfluidic channel was used to ascertain the lowest and highest detectable concentration of analyte of interest simultaneously. The fabrication of PDMS based microfluidic device was carried out as follows.

Briefly, Si master having the microfluidic pattern fabricated by normal photolithography process was used to replicate the microfluidic pattern by molding process. PDMS pre-polymer and curing agent were mixed in 10:1 ratio by weight and mixed well followed by degassing the PDMS mixture under vacuum desiccator for 30 min. The resultant polymer was poured onto the Si master with microfluidic pattern and degassed once again for 30 min before doing the heat treatment at 65° C. overnight in an oven. After the curing step, PDMS chip was peeled off from the Si master and inlet outlet holes were punched.

Example 5: Preparation of PDMS Based Microfluidic Device with Silver Nano-Island (SNI) SERS Substrate Samples The Silver Nano-Island (SNI) was treated with Oxygen plasma along with PDMS microfluidic chip. After plasma treatment, the PDMS chip was mounted on top of the SNI substrate and further heat treated at 100° C. for 1 hr.

Example 6: Preparation of Au Nanoparticle Based SERS Probe Construct

The inventors obtained proteins and their corresponding antibodies from Abcam. Au nanoparticle based SERS probe construct was prepared using the following experimental protocol.

1.93 mL of 60 nm gold colloid (BBI solutions, $2.6 \times 10^{10}$ particles/mL) was treated with 20 µL of 1 mM 4-Aminothiophenol (4-ATP) followed by 50 µL of thiolated PEG with carboxylic acid functional group (RAPP Polymere GmbH) and mixed for 30 min. The resultant gold colloidal mixture was centrifuged at 7000 rpm for 5 min to remove excess unbound 4-ATP and PEG-COOH groups present in the supernatant. The 4-ATP bound gold colloid sediment was reconstituted into 500 µL of double distilled (DD) water. H1N1 antibody was conjugated onto the carboxylic acid functional group of the PEG in presence of EDC/NHS. As a final step, centrifugation of the mixture was carried out at 7000 rpm to remove unbound antibody and reconstitute the gold colloid into 500 µL of DD water.

Similarly, 2-Naphthalene Thiol (2-NT) based gold colloid was prepared using 50 µL, 1 mM 2-NT in 1.9 mL gold colloid followed by addition of 50 µL thiol PEG-COOH and finally conjugated with H5N1 antibody. Antibody for cancer biomarkers such as A1AT and AFP were also bound to 4-ATP and 2-NT following the same protocol described above.

Antibodies were thiolated by means of Pierce Traut's Reagent (2-iminothiolane). Briefly, to each 50 μL of 25 μM antibody, 5 μL of 1 mM Traut's reagent was added including 5 mM EDTA in the buffer to prevent oxidation of sulfhydryl's and the reaction was allowed to happen overnight. The resultant antibody mixture was filtered using Thermo Scientific Zeba Spin Desalting Column by means of centrifugation process to remove non-thiolated antibodies. The thiolated antibody solution was reconstituted to a final volume of 100 μL.

In order to prepare the calibration plot for different biomarkers, the inventors carried out a serial dilution of the protein of interest with DD $H_2O$.

Example 7: Proof of Concept Study on SERS Gradient Microfluidics Device

The as-fabricated gradient microfluidic devices were integrated with SERS active SNI substrates as shown in FIG. 2. It also shows the gradient formation at particular flow rate confirmed by COMSOL simulation depicted in FIG. 3.

As shown in FIG. 3, PDMS and SNI/SNP SERS substrate based microfluidic device may be used to detect and quantify biomolecules through Raman active probes.

Concentration gradient was formed by flowing 10 μM 2-NT in one inlet and 100% pure ethanol in the second inlet. FIG. 4A to FIG. 4D show results of the experiment as a proof of concept study on SERS gradient microfluidics device using 2-NT SERS tag. The inventors observed that 2-NT concentration was highest in Channel 1 and lowest in Channel 5 as shown in FIG. 4C. The results were in close agreement with that of the simulated data.

Example 8: Protein Detection Study

The protein detection study using integrated SERS microfluidic device fabrication part is schematically explained in FIG. 5.

In stage 1 of the experimental process, Au nanoparticle based SERS probes were fabricated with SERS tag and secondary antibody. 4-ATP as SERS tags and A1AT as their corresponding antibody were used by the inventors in the experiments.

In stage 2, SERS microfluidic device was treated with thiolated A1AT primary antibody followed by protein gradient by means of flowing concentrated A1AT protein in one inlet and the buffer for gradient generation.

In the final step, already prepared Au nanoparticle based SERS probe was injected into the SERS microfluidic device.

SERS measurement was carried out after removing the PDMS microfluidic device due to working distance limitations. Several SERS spectra's were collected for concentration gradients and the spectral intensity count was monitored specific to the SERS tags in the study. 1078 $cm^{-1}$ band was used for 4-ATP.

Results were compared to the calibration plot to interpret the final concentration of A1AT protein in each gradient microchannel. FIG. 6 shows the calibration plot prepared using 4-ATP SERS tag for detection and quantification of A1AT cancer biomarker present in the unknown samples. The linear detectable range was found between few tens of nanomolar to sub micromolar. Saturation was observed beyond this range.

In a similar study, SNP based microfluidic device was also tested with the same 4-ATP based SERS tag. All the experimental conditions were the same as previous study except the SERS substrate. FIG. 7 shows the calibration plot for the A1AT protein in SNP based SERS microfluidic device. It was interesting to find that linear regression was much higher for SNP SERS substrate than that of the SNI SERS counterpart. This may be explained by the higher contact point for the primary antibody binding in case of SNP substrate due to presence of three dimensional nanopillar structure than that of SNI substrate which was made up of nanoparticles.

Similarly, the inventors also tested the infectious disease biomarker for influenza H5N1 using a 2-NT based SERS tag, as shown in FIG. 8. The inventors collected multiple SERS spectra, and the spectral intensity count was monitored specific to the SERS tags in this study. 1066 $cm^{-1}$ band corresponding to 2-NT Raman molecule was used. Both FIG. 7 and FIG. 8 were obtained from the SNP derived SERS microfluidic device.

Example 9: Multiplexing

Following the similar experimental setup, multiplexing study was carried out by introducing 3 cross channels into the existing gradient microfluidic design, as shown in FIG. 9. Among the 3, cross microchannel 2 was used for infectious/cancer biomarkers and the 3rd one was used as control to measure the non-specific binding events using BSA protein. The schematic in FIG. 9 provides more details about the experimental flow.

For multiplexing study, as a first step, primary antibody of 2 different biomarkers, in this case A1AT and AFP, were immobilized onto the SERS substrate by flowing the different antibody solution in various microchannel After 30 min incubation, the microchannel was gently washed with DD water for removing unbound antibodies.

As a second step, biofluid/biomolecules of interest were flowed in using both the inlets and allowed to incubate for 30 min. After the incubation step, the SERS microfluidics was washed with continuous flow of buffer solution to remove the unbound/non-specifically bound proteins. This was followed by incubation in 1% BSA solution. BSA occupies the unbound active sites and also the control channel which is devoid of any primary antibody.

After a further washing step, the Au colloid based SERS probe nano-construct was used for protein specific binding event. The chip was used for SERS measurement to detect and quantify the concentration of different protein/biomolecules present in the unknown samples. This concentration was derived from the calibration plot specific to each SERS probe by interpolating the SERS intensity count of the unknown samples.

Upon the successful analysis of detection limit and highest concentration detectable, a new microfluidic design would be used to multiplex detection of multiple, such as 2 to 3, biomarkers simultaneously. The microchannel design is shown in FIG. 10.

Based on the experiments, the inventors were able to successfully carry out simultaneous detection of 2 different biomarkers in the same SERS microfluidic device and get their corresponding concentration gradient. The inventors found that SNP based SERS microfluidics showed higher signal enhancement compared to the SNI based microfluidic setup.

Example 10: Ovarian Cancer Biomarker Haptoglobin (Hp)

The exact reaction scheme Haptoglobin study using peroxidase reaction is shown in FIG. 12.

FIG. 13 shows the Raman spectra for 3,3',5,5'-Tetramethylbenzidine (TMB) and their corresponding product $TMB^{2+}$. In order to avoid the multiple steps involved with the detection and quantification of ovarian cancer biomarker Haptoglobin (Hp), the inventors have integrated all the process steps within a microfluidic platform.

As shown in FIG. 14, a cartridge may be used to pre-pack the chemicals and biologicals required for the peroxidase reaction in sequence by filling them inside chemical resistance polymer tubing with outer diameter ranging from 1 to 1.5 mm. This cartridge consists of known concentration of Hemoglobin (Hb) and known/unknown concentration of Hp for reference/Test sample respectively. This is followed by fixed volume of the peroxidase reactant 3,3',5,5'-Tetramethylbenzidine (TMB) with pre-dissolved $H_2O_2$. An air spacer is generated between Hb/Hb and the TMB mixture in order to avoid any possible mixing. The length of the air spacer depends on the time interval between each Step. Apart from this, acid for quenching the peroxidase reaction and Au colloid for SERS study were also pre-loaded onto the cartridge with the help of air spacer. The overall flow of reaction is given below.

Step 1:

Hb-Hp complex formation between known concentration of Hb and Known/Unknown concentration of Hp depending on the sample type.

Step 2:

Reaction between TMB and Hb-Hp complex in presence of $H_2O_2$

Step 3:

Quenching step involving addition of strong acid such as 0.5 N $H_2SO_4$/1 N HCl into the reaction mixture.

Step 4:

Measuring SERS spectra for the $TMB^{2+}$ product was done either by mixing Au colloid/by means of in-built SERS active substrate present in chamber 4 of the microfluidic device.

Samples and reagents needed for the study were pre-loaded onto the cartridge. The only difference between Test and Reference cartridge is that, in the Test cartridge, only known concentration of Hb to which unknown concentration of Hp will be added. Whereas in Reference cartridge, known concentration of Hb and Hp were preloaded. In the microfluidic designing part, the winding channels present in the microfluidic device is meant for increasing the mixing efficiency of different reagents. Chambers numbered from 1 to 4 corresponds to reagents loaded onto the cartridge in the same order. The size and volume capacity of the chambers were gradually increased staring from step 1 and all the way to step 4 to accommodate the final volume of the reaction mixture.

The experiment was performed by connecting the test and reference cartridge onto the corresponding inlets in the microfluidic device and applying negative pressure on the outlet side by means of attaching a syringe pump at a rate suitable for the reaction. Now Step 1 to step 4 will happen in sequence.

Hence, by means of the above process one can help reduce the multistep reaction into single step and simplify the reaction by performing the reaction on a microfluidic platform.

Example 11: Conclusion

Various embodiments disclosed herein relate to use of a robust, reliable and reproducible SERS active planar substrates (Silicon/Glass based Silver Nano-islands (SNI) and Silicon Nanopillar (SNP)) with high sensitivity for integration into microfluidic devices. Demonstration of multiplexing was carried out in an integrated SERS microfluidics.

The antibody may be directly attached onto the SERS active substrate without any linker agent which increases the spacing between Raman reporter molecule and SERS substrate. The microfluidic design is unique for this study, and has minor variations from the existing designs.

Application for simultaneous detection and quantification of various cancer biomarkers such as A1AT and AFP was demonstrated. Applicability of SERS microfluidics in detection and quantification of infectious disease biomarker H5N1 was also demonstrated.

Apart from the above, the SERS microfluidic platform disclosed herein may also be used for detection and quantification of ovarian cancer biomarker Haptoglobin (Hp), whereby the design suggested for Hp study is completely novel.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A biosensor for the detection of an analyte using surface-enhanced Raman spectroscopy (SERS), the biosensor comprising a SERS-active substrate and a microfluidic circuit device arranged to be in fluid communication with the SERS-active substrate, wherein the microfluidic circuit device comprises a concentration gradient generator having two or more mixing structures and (i) at least two inlets and (ii) at least two outlets, wherein a plurality of respective microchannels extend from each of the at least two outlets of the concentration gradient generator, and wherein the microfluidic circuit device further comprises at least one cross-flow line intersecting with and in fluid communication with each of the microchannels, wherein each of the at least one cross-flow line has an inlet for introducing an analyte binding molecule into the microfluidic circuit device, wherein each of the at least one cross-flow line which intersects with each of the microchannels defines respective reaction chambers in which a reaction between said analyte binding molecule and a sample from one of the at least two inlets occurs, and wherein the SERS-active substrate is comprised in or forms at least a portion of each of the reaction chambers.

2. The biosensor according to claim 1, wherein the SERS-active substrate is a support comprising at least one SERS-active nanostructure disposed on a surface of the support.

3. The biosensor according to claim 2, wherein the support comprising at least one SERS-active nanostructure disposed on a surface of the support is a dielectric support comprising a plurality of nano-islands coated with a layer of a SERS-active material disposed on a surface of the support.

4. The biosensor according to claim 2, wherein the support comprising at least one SERS-active nanostructure disposed on a surface of the support is a semiconductor support comprising a plurality of nanopillars coated with a layer of a SERS-active material on a surface of the support.

5. The biosensor according to claim 2, wherein the support comprising at least one SERS-active nanostructure disposed on a surface of the support is a paper support comprising a plurality of nanoparticles of a SERS-active material attached to a surface of the support.

6. The biosensor according to claim 2, wherein the microfluidic circuit device is disposed on the SERS-active substrate so that at least a portion of the microfluidic circuit device is in fluid communication with the surface of the support comprising at least one SERS-active nanostructure.

7. The biosensor according to claim 2, wherein the microfluidic circuit device is removably attached to the SERS-active substrate.

8. The biosensor according to claim 1, wherein the SERS-active substrate comprises nanoparticles of a SERS-active material.

9. The biosensor according to claim 1, wherein the SERS-active substrate further comprises at least one analyte binding molecule attached thereto.

10. A method of manufacturing a biosensor for the detection of an analyte using surface-enhanced Raman spectroscopy (SERS) according to claim 1, the method comprising
 a) providing a SERS-active substrate, and
 b) arranging a microfluidic circuit device to be in fluid communication with the SERS-active substrate to obtain the biosensor.

11. A method for detecting at least one analyte using surface enhanced Raman spectroscopy (SERS), the method comprising
 a) providing a biosensor according to claim 1;
 b) introducing at least one analyte binding molecule to the microfluidic circuit device to attach the at least one analyte binding molecule on the SERS-active substrate;
 c) introducing one or more analytes to the microfluidic circuit device to contact the at least one analyte binding molecule with the one or more analytes;
 d) detecting a surface enhanced Raman signal from the SERS-active substrate; and
 e) checking the obtained signal against a reference to correlate the obtained signal with the amount of the one or more analytes.

12. The method according to claim 11, wherein the one or more analytes are selected from the group consisting of proteins, peptides, nucleic acids, carbohydrates, lipids, cells, viruses, small molecules, and combinations thereof.

13. The method according to claim 11, further comprising introducing a further SERS-active substrate to the microfluidic circuit device after step c).

14. The method according to claim 13, wherein the further SERS-active substrate comprises a further analyte binding molecule, a Raman-active marker compound and a metallic nanoparticle, wherein the further analyte binding molecule and the Raman-active marker compound are independently covalently attached to the metallic nanoparticle.

15. The method according to claim 14, wherein the further analyte binding molecule is the same as or different from the analyte binding molecule.

16. The method according to claim 11, wherein the reference is generated using the microfluidic circuit device and expresses intensity of SERS signal as a function of analyte concentration.

17. The method according to claim 11, wherein the method is a multiplex method for detecting more than one analyte, wherein more than one type of analyte binding molecules are introduced to the microfluidic circuit device.

18. A method for detecting haptoglobin (Hp) using surface enhanced Raman spectroscopy (SERS), the method comprising
 a) providing a biosensor according to claim 1;
 b) introducing a first mixture comprising haemoglobin and a sample suspected to comprise haptoglobin to the microfluidic circuit device;
 c) introducing a peroxidase substrate and a peroxide source to the microfluidic circuit device and contacting with the first mixture to form a second mixture;
 d) introducing a quenching agent to the microfluidic circuit device and contacting with the second mixture to form a third mixture;
 e) contacting the third mixture with the SERS-active substrate; and
 f) detecting a surface enhanced Raman signal from the SERS-active substrate.

* * * * *